United States Patent
Viola et al.

(10) Patent No.: US 10,449,168 B2
(45) Date of Patent: Oct. 22, 2019

(54) POTENT PHTHALATE INHIBITORS OF ASPARTATE N-ACETYLTRANSFERASE AND SELECTIVE ASPARTATE PATHWAY INHIBITORS

(71) Applicant: The University of Toledo, Toledo, OH (US)

(72) Inventors: Ronald E. Viola, Toledo, OH (US); Bharani Thangavelu, Toledo, OH (US); Vinay Mutthamsetty, Toledo, OH (US); Qinzhe Wang, Toledo, OH (US); Pravin Bhansali, Toledo, OH (US)

(73) Assignee: The University of Toledo, Toledo, OH (US)

( * ) Notice: Subject to any disclaimer, the term of this patent is extended or adjusted under 35 U.S.C. 154(b) by 0 days.

(21) Appl. No.: 15/755,447

(22) PCT Filed: Aug. 29, 2016

(86) PCT No.: PCT/US2016/049208
§ 371 (c)(1),
(2) Date: Feb. 26, 2018

(87) PCT Pub. No.: WO2017/040376
PCT Pub. Date: Mar. 9, 2017

(65) Prior Publication Data
US 2018/0250252 A1      Sep. 6, 2018

Related U.S. Application Data

(60) Provisional application No. 62/212,149, filed on Aug. 31, 2015, provisional application No. 62/314,691, filed on Mar. 29, 2016.

(51) Int. Cl.
*A61K 31/198* (2006.01)
*C07C 229/38* (2006.01)
(Continued)

(52) U.S. Cl.
CPC ............ *A61K 31/198* (2013.01); *A61P 25/28* (2018.01); *A61P 31/00* (2018.01); *C07C 227/18* (2013.01);
(Continued)

(58) Field of Classification Search
CPC .......................... A61K 31/198; C07C 229/38
See application file for complete search history.

(56) References Cited

U.S. PATENT DOCUMENTS

2008/0214615 A1    9/2008   Muller et al.
2015/0219654 A1    8/2015   Naleway et al.

OTHER PUBLICATIONS

Wolff, Manfred E. "Burger's Medicinal Chemistry, 5ed, Part I", John Wiley & Sons, 1995, pp. 975-977.*
(Continued)

*Primary Examiner* — Valerie Rodriguez-Garcia
(74) *Attorney, Agent, or Firm* — MacMillan, Sobanski & Todd, LLC

(57) ABSTRACT

Phthalate derivatives that are aspartate-P-semialdehyde dehydrogenase (ASADH) inhibitor compounds, aspartate N-acetyltransferase (ANAT) inhibitor compounds, or both, are described, as well as methods of making the same, and methods of using the same.

14 Claims, 11 Drawing Sheets
(3 of 11 Drawing Sheet(s) Filed in Color)

$K_i = 150 \ \mu M$ $K_i = 98 \ \mu M$ $K_i = 79 \ \mu M$ $K_i = 38 \ \mu M$ $K_i = 34 \ \mu M$ $K_i = 29 \ \mu M$

(51) Int. Cl.
- *A61P 25/28* (2006.01)
- *A61P 31/00* (2006.01)
- *C07C 227/18* (2006.01)

(52) U.S. Cl.
CPC ........... *C07C 229/38* (2013.01); *Y02A 50/475* (2018.01); *Y02A 50/481* (2018.01)

(56) References Cited

OTHER PUBLICATIONS

Banker et al, "Modern Pharmaceutics, 3ed.", Marcel Dekker, New York, 1996, pp. 451 and 596.*
Jordan, V. C. Nature Reviews: Drug Discovery, 2, 2003, pp. 205-213.*
Dörwald, F. Zaragoza. Side Reactions in Organic Synthesis: A Guide to Successful Synthesis Design, Weinheim: WILEY-VCH Verlag GmbH & Co. KGaA, 2005, Preface.*
NIH Canavan Disease information page provided herein—downloaded Nov. 15, 2018.*
B. Rodriguez-Spong et al. (Advanced Drug Delivery Reviews, 2004, 56, p. 263).*
AKOS007518496, PubChem, Compound Summary for CID 56186451, 2012, pp. 1-11.
Pavlovsky et al., "A cautionary tale of structure—guided inhibitor development against an essential enzyme in the aspartate-biosynthetic pathway", Research Gate, 2014, pp. 1-38.
Thangavelu et al., "Elaboration of a fragment library hit produces potent and selective aspartate semialdehyde lehydrogenase inhibitors", Bioorganic & Medicinal Chemistry, 2015, vol. 23, pp. 662-6631.
PCT International Search Report and the Written Opinion, Application No. PCT/US2016/049208 filed Aug. 29, 2016, dated Nov. 14, 2016.

* cited by examiner

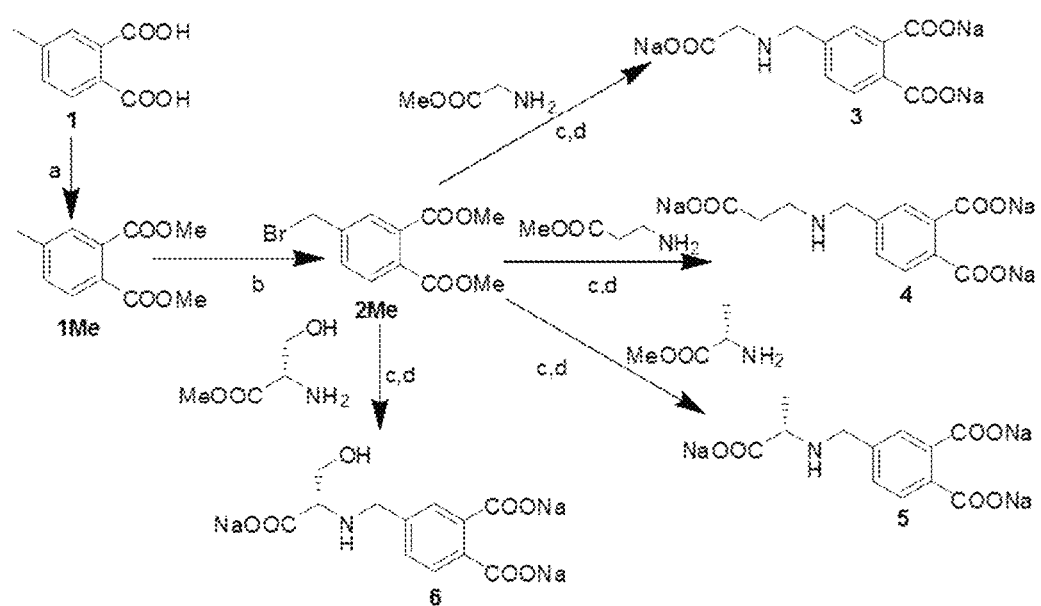
FIG. 2A – Scheme 1A

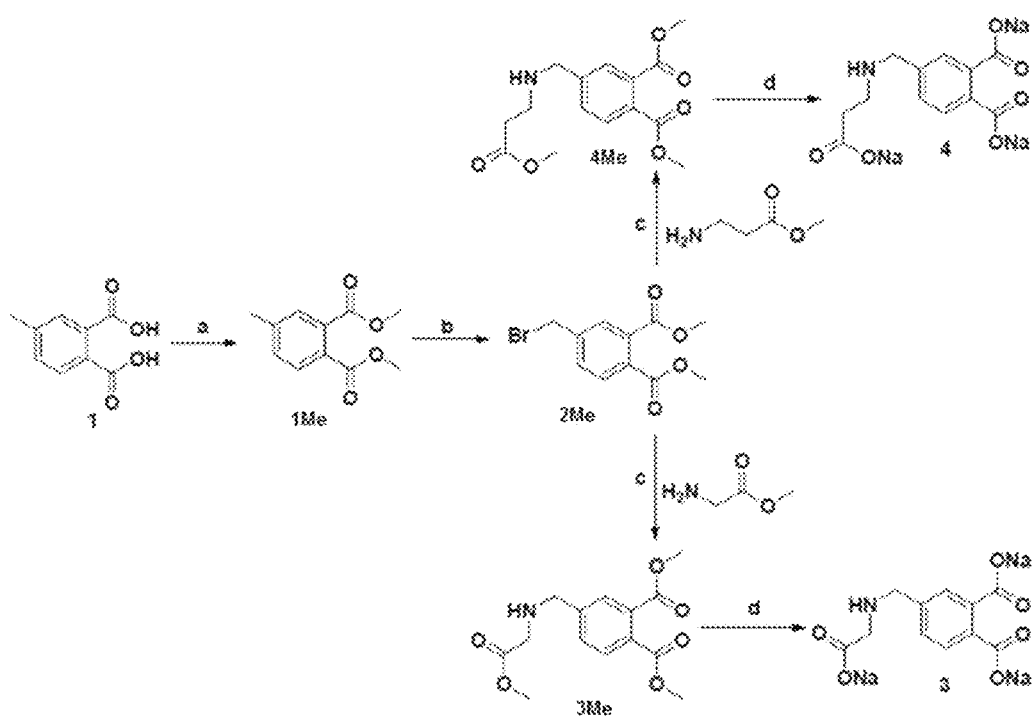
FIG. 2B – Scheme 1B

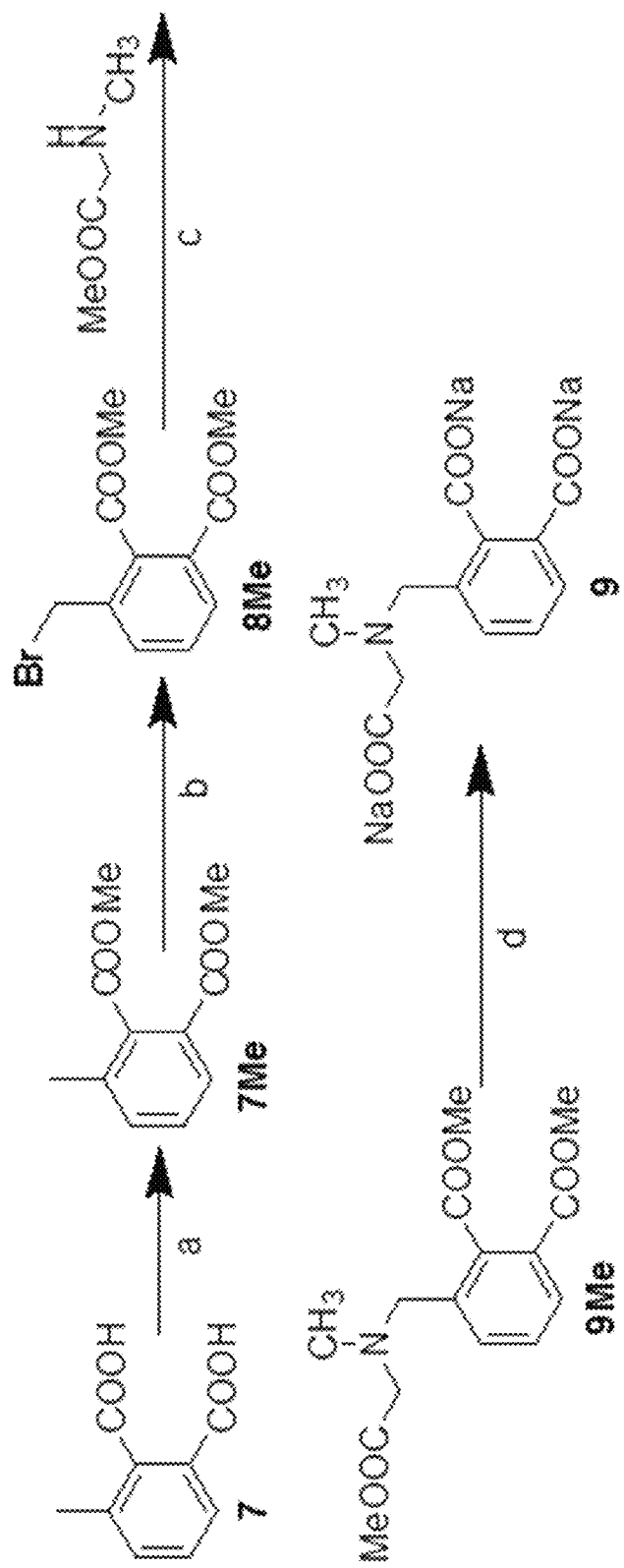
FIG. 3 – Scheme 2

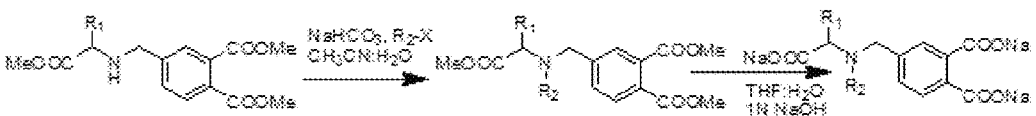
| compd | $R_1$ | $R_2$ | $K_i(\mu M)$ spASADH | vcASADH |
|---|---|---|---|---|
| 3 | H | H | 246 ± 20 | 528 ± 32 |
| 4[a] | H | H | 2400 ± 180 | n.i.[b] |
| 5 | (S)-CH$_3$ | H | 296 ± 26 | 609 ± 23 |
| 6 | (S)-CH$_2$OH | H | 324 ± 24 | 654 ± 22 |
| 10 | H | CH$_3$ | 296 ± 36 | 675 ± 54 |
| 11 | H | allyl | 303 ± 22 | 663 ± 36 |
| 12 | H | propionitrile | 220 ± 14 | 498 ± 27 |
| 13 | H | benzyl | 297 ± 14 | 696 ± 33 |
| 14 | H | 1-naphthyl | 396 ± 42 | 749 ± 54 |
| 15 | H | 2-naphthyl | 329 ± 22 | 724 ± 47 |
| 16 | H | N-ethylmorpholino | 176 ± 22 | 692 ± 39 |
| 17 | H | 4-biphenyl | 12 ± 1.2 | 634 ± 29 |
| 37 | H | acetaldehyde | 276 ± 16 | 655 ± 51 |
FIG. 4 – Table 1

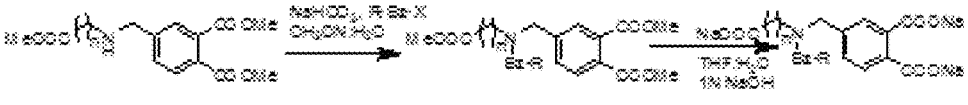
FIG. 5 – Table 2

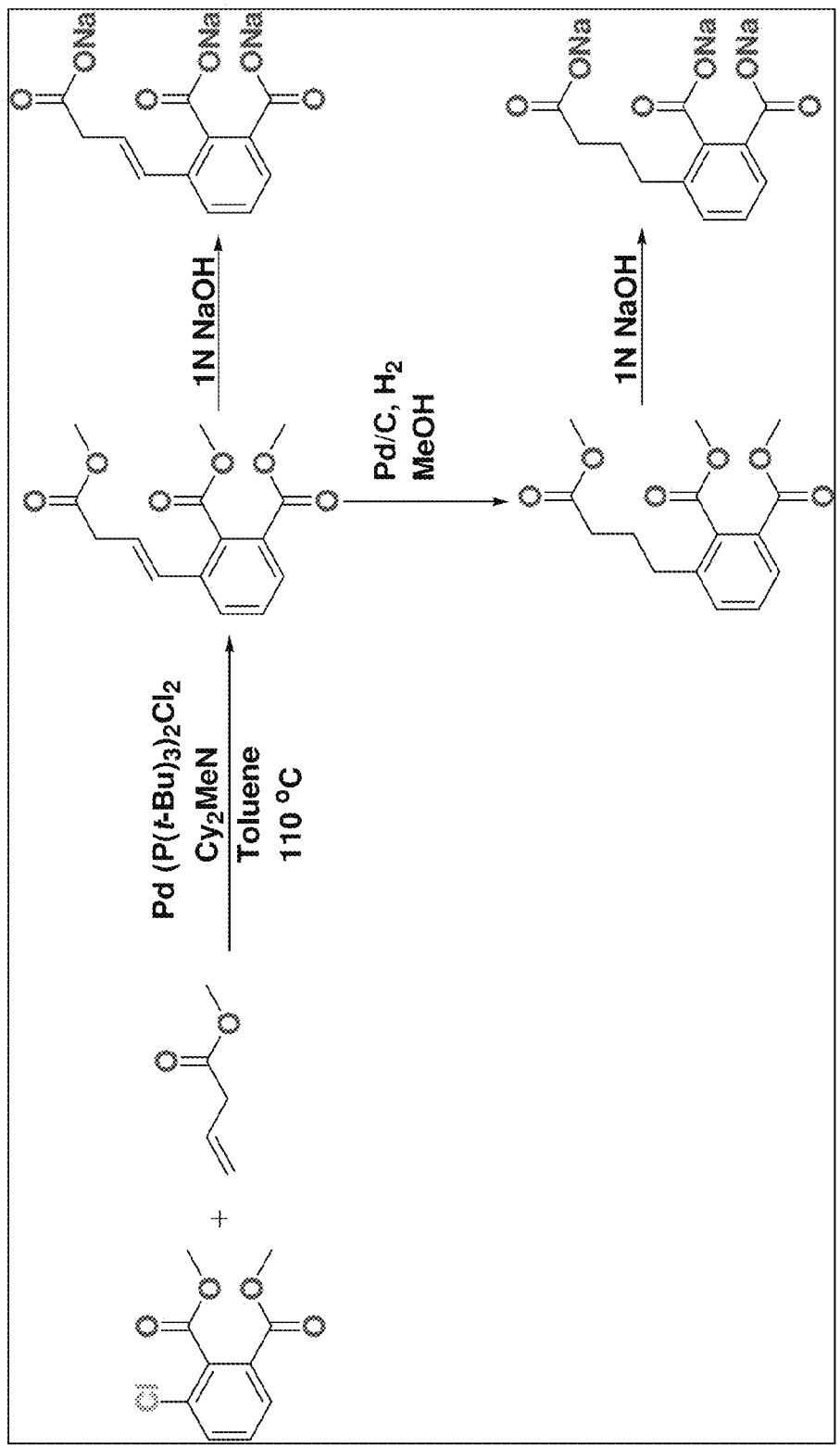
FIG. 6 – Scheme 3

Table 3: Summary of Compound Library Screening against ANAT

| Library | compounds | moderate inhibitors* | strong inhibitors* | Most potent ($K_i$) |
|---|---|---|---|---|
| Amino acids | 96 | 3 | 0 | N-chloroacetyl-L-aspartic acid ($K_i$ = 200 μM) |
| Metabolites | 96 | 13 | 0 | 2-bromofumarate ($K_i$ = 367 μM) |
| Amino acids II | 64 | 1 | 0 | N-alanyl-L-aspartic acid ($K_i$ = 1.6 mM) |
| Constrained analogs | 77 | 5 | 1 | N-carbobenzyloxy-L-aspartic acid ($K_i$ = 17 μM) |
| Synthesized dioic acids | 68 | 24 | 6 | N-carbobenzyloxy-L-glutamic acid ($K_i$ = 12 μM) N-(1-oxo-3-phenylpropyl)-L-aspartic acid ($K_i$ = 31 μM) |
| Synthesized phthalates | 50 | 23 | 9 | 4-aminomethyl(N-carboethyl,N-p-carboxybenzyl) phthalate ($K_i$ = 29 μM) |
| TOTAL | 451 | 69 | 16 | |
| Hit rate | | 15% | 3.5% | |

\* at least 50% inhibition when tested at 2 mM concentration
compounds with $K_i$ values less than 200 μM

FIG. 7 – Table 3

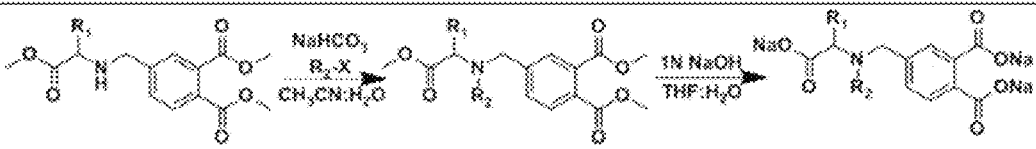
FIG. 8 – Table 4

Table 5: Synthesis and kinetic evaluation of 4-(N-substituted)benzylaminoalkylphthalates

| Compound[a] | R | $K_i$ (µM) |
|---|---|---|
| 21 | 2-methyl | 1404 ± 260 |
| 22 | 3-methyl | 1702 ± 223 |
| 23 | 4-methyl | 4234 ± 769 |
| 43* | 2-methyl | 724 ± 91 |
| 44* | 3-methyl | 563 ± 89 |
| 45* | 4-methyl | 2749 ± 449 |
| 18 | 2-bromo | 114 ± 15 |
| 19 | 3-bromo | 269 ± 31 |
| 20 | 4-bromo | 1195 ± 53 |
| 53* | 2-bromo | 173 ± 21 |
| 54* | 3-bromo | 101 ± 4 |
| 35* | 4-bromo | 370 ± 60 |
| 24 | 2-trifluoromethyl | 390 ± 50 |
| 25 | 3-trifluoromethyl | 104 ± 9 |
| 26 | 4-trifluoromethyl | 791 ± 51 |
| 40* | 2-trifluoromethyl | 88 ± 6 |
| 41* | 3-trifluoromethyl | 37 ± 1 |
| 36* | 4-trifluoromethyl | 186 ± 16 |
| 27 | 2-trifluoromethoxy | 464 ± 50 |
| 28 | 3-trifluoromethoxy | 246 ± 39 |
| 29 | 4-trifluoromethoxy | 749 ± 88 |
| 30 | 4-difluoromethoxy | 489 ± 90 |
| 33 | 4-tert-butyl | 687 ± 66 |
| 34 | 4-(2-perfluoropropyl) | 426 ± 68 |
| 46* | 4-tert-butyl | 1660 ± 326 |
| 47* | 4-(2-perfluoropropyl) | 587 ± 72 |
| 31 | 4-carboxy | 104 ± 9 |
| 50* | 4-carboxy | 29 ± 2 |
| 32 | 4-carboxamide | 1884 ± 380 |
| 52 | 4-acetyl | 2541 ± 219 |
| 51* | 4-carboxy-1-napthyl | 187 ± 22 |

[a] n = 1, except * where n = 2
[b] no inhibition observed at concentrations up to 2 mM

FIG. 9 – Table 5

POTENT PHTHALATE INHIBITORS OF ASPARTATE N-ACETYLTRANSFERASE AND SELECTIVE ASPARTATE PATHWAY INHIBITORS

RELATED APPLICATIONS

This application is a national stage application filed under 35 U.S.C. § 371 of international application PCT/US2016/049208, filed under the authority of the Patent Cooperation Treaty on Aug. 29, 2016, which claims priority to U.S. Provisional Application No. 62/212,149, filed under 35 U.S.C. § 111(b) on Aug. 31, 2015, as well as U.S. Provisional Application No. 62/314,691, filed under 35 U.S.C. § 111(b) on Mar. 29, 2016. The disclosures of all the aforementioned applications are incorporated herein by reference in their entirety.

STATEMENT REGARDING FEDERALLY SPONSORED RESEARCH

This invention was made with government support under Grant Number AI077720 awarded by the National Institutes of Health. The government has certain rights in this invention.

BACKGROUND OF THE INVENTION

Resistance to drugs, such as antibiotics, is a serious problem. Drug resistance is limiting the effectiveness of most currently used antimicrobial agents. Infectious organisms are becoming resistant to even the most recently developed antimicrobials that target essential steps in cell wall assembly and protein biosynthesis. Thus, there is a need in the art for new antimicrobials with different modes of action.

Most current antimicrobials target either cell wall biosynthesis or DNA replication. The higher population of microbes that have developed resistance to the available front-line antibiotics requires new drug molecules which can act through different mechanisms to thwart this developing resistance. Finding and validating new targets offers the best hope of finding new drugs with different modes of action. Furthermore, introducing species-selectivity can further delay the development of drug resistance. It would therefore be advantageous to develop new antimicrobial drugs that are species selective and act through a mechanism other than by targeting cell wall biosynthesis or DNA replication.

SUMMARY OF THE INVENTION

Described are various phthalate compounds, useful as inhibitors either aspartate-β-semialdehyde dehydrogenase (ASADH), aspartate N-acetyltransferase (ANAT), or both.

In a first aspect, provided herein is a compound having Formula I:

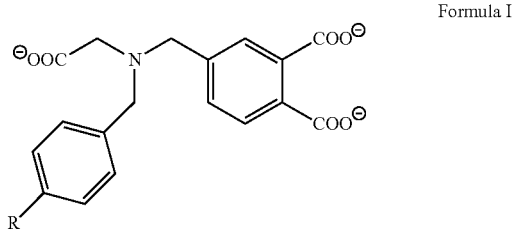

Formula I where R is hydrophobic. Also provided are salts, stereoisomers, prodrugs, racemates, solvates, hydrates, and polymorphs thereof. The compounds of Formula I are ASADH inhibitor compounds.

In certain embodiments of the ASADH inhibitor compounds, R is hydrogen, a straight or branched alkane having from 1 to 6 carbons, a halogen, a halogenated alkane having from 1 to 6 carbons, a halogenated alkoxy, or a substituted or unsubstituted cyclic alkane. In certain embodiments, R is selected from the group consisting of: H, 4-bromo, 4-methyl, 4-trifluoromethyl, 4-trifluoromethoxy, 4-difluoromethoxy, 4-tert-butyl, 4-(2-perfluoropropyl), 4-phenyl, 4-((2-benzyl)vinyl), and 4-trifluoromethyl. In certain embodiments, R is 4-phenyl or 4-(2-perfluoropropyl).

In certain embodiments, the ASADH inhibitor compound is a methyl triester. In certain embodiments, the ASADH inhibitor compound is a sodium salt.

In certain embodiments, the ASADH inhibitor compound is selected from the group consisting of: N-carboxymethyl-3,4-dicarboxybenzylamine; N-carboxyethyl-3,4-dicarboxybenzylamine; N-((2-methyl)carboxymethyl)-3,4-dicarboxybenzylamine; N-((2-hydroxymethyl)carboxymethyl)-3,4-dicarboxybenzylamine; N-methyl, N-carboxymethyl-2,3-dicarboxybenzylamine; N-methyl, N-carboxymethyl-3,4-dicarboxybenzylamine; N-allyl, N-carboxymethyl-3,4-dicarboxybenzylamine; N-acetonitrile, N-carboxymethyl-3,4-dicarboxybenzylamine; N-benzyl, N-carboxymethyl-3,4-dicarboxybenzylamine; N-(1-naphthyl)-N-carboxymethyl-3,4-dicarboxybenzylamine; N-(2-naphthyl)-N-carboxymethyl-3,4-dicarboxybenzylamine; N-(ethylmorpholino)-N-carboxymethyl-3,4-dicarboxybenzylamine; N-(4-biphenyl)-N-carboxymethyl-3,4-dicarboxybenzylamine; N-(2-bromobenzyl)-N-carboxymethyl-3,4-dicarboxybenzylamine; N-(3-bromobenzyl)-N-carboxymethyl-3,4-dicarboxybenzylamine; N-(4-bromobenzyl)-N-carboxymethyl-3,4-dicarboxybenzylamine; N-(2-methylbenzyl)-N-carboxymethyl-3,4-dicarboxybenzylamine; N-(3-methylbenzyl)-N-carboxymethyl-3,4-dicarboxybenzylamine, N-(4-methylbenzyl)-N-carboxymethyl-3,4-dicarboxybenzylamine; N-(2-trifluoromethylbenzyl)-N-carboxymethyl-3,4-dicarboxybenzylamine; N-(3-trifluoromethylbenzyl)-N-carboxymethyl-3,4-dicarboxybenzylamine; N-(4-trifluoromethylbenzyl)-N-carboxymethyl-3,4-dicarboxybenzylamine; N-(2-trifluoromethyoxybenzyl)-N-carboxymethyl-3,4-dicarboxybenzylamine; N-(3-trifluoromethoxybenzyl)-N-carboxymethyl-3,4-dicarboxybenzylamine; N-(4-trifluoromethoxybenzyl)-N-carboxymethyl-3,4-dicarboxybenzylamine; N-(4-difluoromethoxybenzyl)-N-carboxymethyl-3,4-dicarboxybenzylamine; N-(4-carboxybenzyl)-N-carboxymethyl-3,4-dicarboxybenzylamine; N-(4-carboxamidebenzyl)-N-carboxymethyl-3,4-dicarboxybenzylamine; N-(4-t-butylbenzyl)-N-carboxymethyl-3,4-dicarboxybenzylamine; N-(4-(2-perfluoropropyl))-N-carboxymethyl-3,4-dicarboxybenzylamine; N-(4-bromobenzyl)-N-carboxyethyl-3,4-dicarboxybenzylamine; N-(4-trifluoromethylbenzyl)-N-carboxymethyl-3,4-dicarboxybenzylamine; and N-acetal-N-carboxymethyl-3,4-dicarboxybenzylamine.

Also provided is a method of making a compound described herein, the method involving the steps of esterifying a dicarboxylic methylphthalate to produce a methylphthalate dimethyl ester; bromonating the methylphthalate dimethyl ester to produce a bromomethylphthalate dimethyl ester; and reacting the bromomethylphthalate dimethyl ester with an alkyl halide or a benzyl halide to produce an ester compound described herein. In certain embodiments, the method further includes base-hydrolyzing the ester compound to produce a salt compound.

Also provided is a method of making a compound described herein, the method involving the steps of esterifying a dicarboxylic methylphthalate to produce a methylphthalate dimethyl ester; bromonating the methylphthalate dimethyl ester to produce a bromomethylphthalate dimethyl ester; and coupling the bromomethylphthalate dimethyl ester with glycine methyl ester to produce an esterified N-carboxymethyl dicarboxybenzylamine. In certain embodiments, the method further includes base-hydrolyzing the esterified N-carboxymethyl dicarboxybenzylamine to produce a salt compound.

Also provided is a method of making a compound described herein, the method involving the steps of esterifying a dicarboxylic methylphthalate to produce a methylphthalate dimethyl ester; bromonating the methylphthalate dimethyl ester to produce a bromomethylphthalate dimethyl ester; and coupling the bromomethylphthalate dimethyl ester with β-alanine methyl ester to produce an esterified N-carboxyethyl dicarboxybenzylamine. In certain embodiments, the method further includes base-hydrolyzing the esterified N-carboxyethyl dicarboxybenzylamine to produce a salt compound.

Also provided is a pharmaceutical composition that includes a compound described herein and a pharmaceutically acceptable excipient, diluent, or carrier.

Also provided is a method of treating an infection, the method involving administering an effective amount of an ASADH inhibitor compound described herein to a patient having an infection to treat the infection. In certain embodiments, the ASADH inhibitor compound is administered as a prodrug. In particular embodiments, the prodrug is a methyl ester prodrug. In certain embodiments, the infection is from a multidrug-resistant pathogen. In particular embodiments, the multidrug-resistant pathogen is selected from the group consisting of: *Streptococcus pneumoniae*, drug-resistant *Campylobacter*, drug-resistant *Neisseria gonorrhoeae*, drug-resistant nontyphoidal *Salmonella*, methicillin-resistant *Staphylococcus aureus* (MRSA), drug-resistant *Shigella*, extended-spectrum β-lactamase (ESBL)-producing Enterobacteriaceae, vancomycin-resistant *Enterococcus* (VRE), carbapenem-resistant Enterobacteriaceae (CRE), and *Clostridium difficile*.

Also provided is a method of blocking the aspartate pathway in a pathogen, the method involving exposing cells of a pathogen to an effective amount of an ASADH inhibitor compound described herein to inhibit aspartate-β-semialdehyde dehydrogenase, and blocking the aspartate pathway in the pathogen. In certain embodiments, the compound inhibits the production of aspartate semialdehyde (ASA) in the pathogen. In certain embodiments, the ASADH inhibitor compound inhibits the production of S-adenosyl methionine (AdoMet) in the pathogen. In certain embodiments, the ASADH inhibitor compound inhibits the production of 4,5-dihydroxy-2,3-pentanedione and/or acyl homoserine lactones. In certain embodiments, the ASADH inhibitor compound interferes with quorum sensing by the pathogen. In certain embodiments, the ASADH inhibitor compound interferes with the assembly of a biofilm polysaccharide matrix in the pathogen.

Also provided is a kit for preparing an ASADH inhibitor compound, the kit including a first container housing a bromomethylphthalate dimethyl ester, and a second container housing either an alkyl halide or a benzyl halide. In certain embodiments, the kit further includes a pharmaceutically acceptable excipient, diluent, or carrier.

In a second aspect, provided herein is a compound having Formula II:

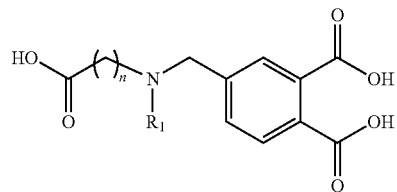

Formula II where n is either 1 or 2, and $R_1$ is substituted or unsubstituted aryl, alkyl, aralkyl, or aryloxy. Also provided are salts, stereoisomers, prodrugs, racemates, solvates, hydrates, and polymorphs thereof. The compounds of Formula II are ANAT inhibitor compounds.

In certain embodiments, $R_1$ comprises benzyl. In certain embodiments, $R_1$ comprises naphthyl. In certain embodiments, n is 1, and $R_1$ comprises naphthyl. In certain embodiments, n is 2, and $R_1$ comprises naphthyl. In certain embodiments, $R_1$ comprises biphenyl.

In certain embodiments, the compound comprises Formula III:

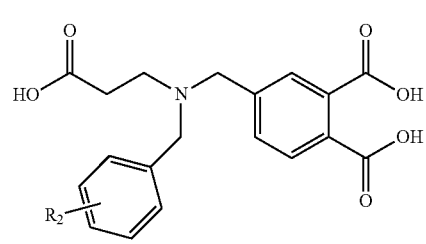

Formula III where $R_2$ is halo or substituted or unsubstituted aryl, alkyl, or carboxyl, provided that when $R_2$ is aryl, the aryl is in a fused bicyclic ring.

In certain embodiments, $R_2$ is substituted with one or more halogens. In certain embodiments, $R_2$ is trifluoro substituted. In certain embodiments, $R_2$ is phenyl. In certain embodiments, $R_2$ is bromo. In certain embodiments, $R_2$ is a para-substituent. In certain embodiments, $R_2$ is an ortho-substituent.

In certain embodiments, the compound is compound (50):

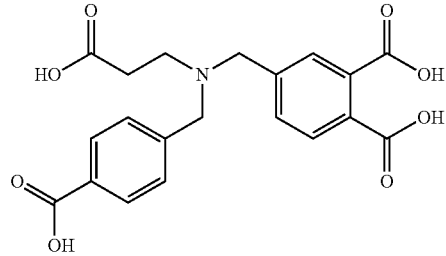

(50)

In certain embodiments, the compound is compound (49):

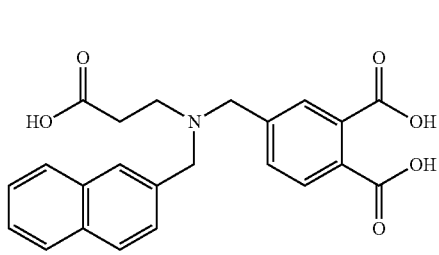

(49)

In certain embodiments, the compound is compound (41):

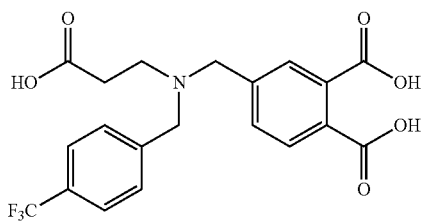

(41)

In certain embodiments, the compound is compound (54):

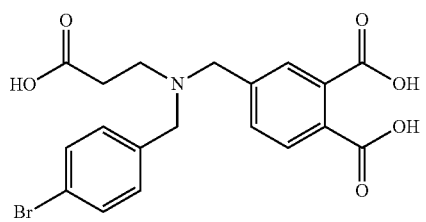

(54)

In certain embodiments, the compound is compound (40):

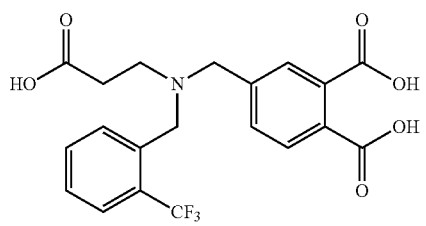

(40)

In certain embodiments, the compound is compound (53):

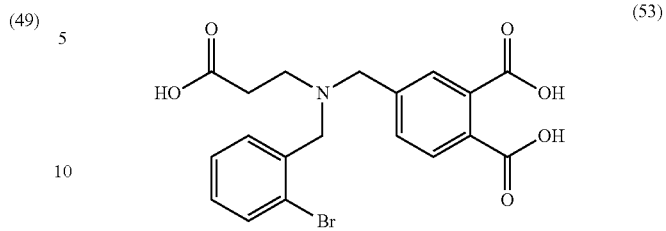

(53)

Also provided is a pharmaceutical composition comprising an effective amount of a compound of Formula II, and a pharmaceutically acceptable excipient, diluent, or carrier.

Also provided is a method of inhibiting ANAT activity in a cell, the method comprising administering an effective amount of a compound of Formula II to a cell, and inhibiting ANAT activity in the cell. In certain embodiments, the cell is a brain cell. In particular embodiments, the cell is in a human subject.

Also provided is a method for treating, preventing, or ameliorating Canavan disease, the method comprising administering an effective amount of a compound of Formula II to a patient in need thereof, and treating, preventing, or ameliorating Canavan disease.

Also provided is a kit for preparing an ANAT inhibitor compound, the kit comprising a first container housing a methylphthalate dimethyl ester, and a second container housing either an alkyl halide or a benzyl halide.

BRIEF DESCRIPTION OF THE DRAWINGS

The patent or application file may contain one or more drawings executed in color and/or one or more photographs. Copies of this patent or patent application publication with color drawing(s) and/or photograph(s) will be provided by the U.S. Patent and Trademark Office upon request and payment of the necessary fees.

FIGS. 2A-2B: Schemes 1A and 1B, showing the synthesis of 4-aminomethylphthalate derivatives. Scheme 1B shows an expanded version of Scheme 1A for compounds 3 and 4. Reagents and conditions for both schemes: (a) $H_2SO_4$/MeOH, μwave, 80° C., 8 h; (b) NBS/DCM, light, 3 h; (c) $NaHCO_3$/DMF, r.t., 8 h; (d) 1 N NaOH, r.t., 3 h.

FIG. 3: Scheme 2, showing the synthesis of 3-aminomethylphthalate derivatives. Reagents and conditions: (a) $H_2SO_4$/MeOH, μwave, 80° C., 8 h; (b) NBS/DCM, light, 3 h; (c) $NaHCO_3$/DMF, r.t., 8 h; (d) 1 N NaOH, r.t., 3 h.

FIG. 4: Table 1, showing the synthesis and kinetic evaluation of 4-aminomethylphthalate derivatives. [a]N-carboxylmethyl group replaced with N-carboxyethyl. [b]No inhibition observed at concentrations up to 2 mM.

FIG. 5: Table 2, showing the synthesis and kinetic evaluation of 4-(N-substituted)benzylaminoalkylphthalates. [a]n=1 for all entries, except * where n=2. [b]No inhibition observed at concentrations up to 4 mM.

FIG. 6: Scheme 3, shown the synthesis of 3-(3-carboxypropyl)phthalate and 3-(2-carboxyethyl)phthalate using Heck coupling reactions.

FIG. 7: Table 3, summarizing the results of screening a compound library against ANAT.

FIG. 8: Table 4, showing the synthesis and kinetic evaluation of 4-aminomethylphthalate and 4-aminoethylphthalate derivatives.

FIG. 9: Table 5, showing the synthesis and kinetic evaluation of 4-(N-substituted)benzylaminoalkylphthalates.

DETAILED DESCRIPTION OF THE INVENTION

Figure 1:
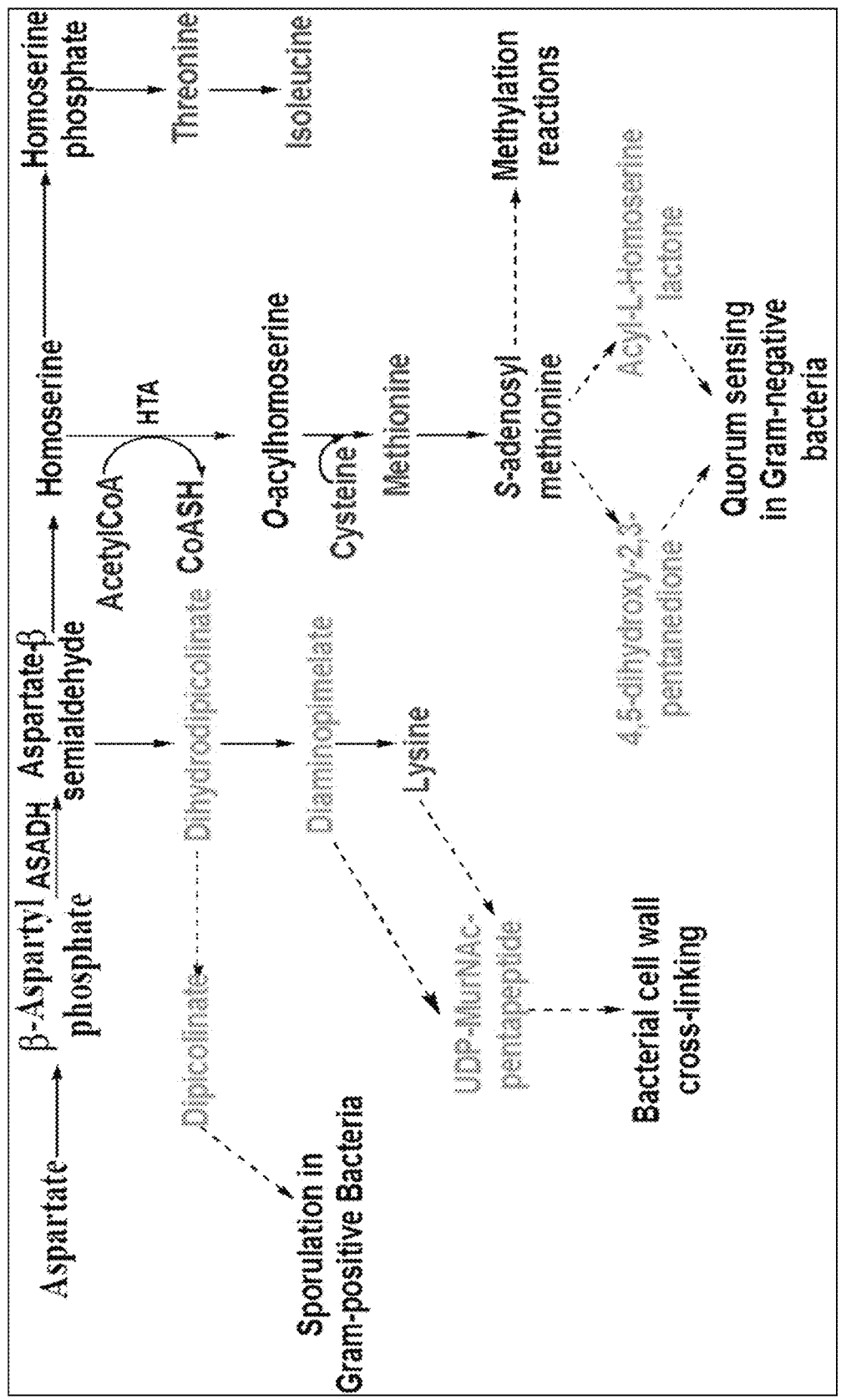
FIG. 1: Diagram of the aspartate metabolic pathway.

Throughout this disclosure, various publications, patents, and published patent specifications are referenced by an identifying citation. The disclosures of these publications, patents, and published patent specifications are hereby incorporated by reference into the present disclosure in their entirety to more fully describe the state of the art to which this invention pertains.

Definitions

For convenience, various terms used herein are defined prior to further description of the various embodiments of the present disclosure.

Unless stereochemistry is specifically indicated, all stereoisomers of the compounds herein are included, as pure compounds as well as mixtures thereof.

The term "composition" as used herein is intended to encompass a product comprising the specified ingredients in the specified amounts, as well as any product that results, directly or indirectly, from combinations of the specified ingredients in the specified amounts.

The term "protecting group" as used herein refers to a group which is introduced onto a functional group in a compound and which modifies that functional group's chemical reactivity. Typically, the protecting group modifies the functional group's chemical activity in such a way that it renders the functional group chemically inert to the reaction conditions used when a subsequent chemical transformation is effected on the compound.

The term "alkyl" refers to monovalent alkyl groups having from 1 to 50 carbon atoms, preferably having from 1 to 10 carbon atoms, and more preferably having from 1 to 6 carbon atoms. This term is exemplified by groups such as methyl, ethyl, n-propyl, iso-propyl, n-butyl, iso-butyl, n-hexyl, and the like. "Substituted alkyl" refers to an alkyl group, preferably of from 1 to 10 carbon atoms, having from 1 to 3 substituents selected from the group consisting of alkoxy, substituted alkoxy, acyl, acylamino, amino, aminoacyl, aminocarboxy esters, cyano, cycloalkyl, halogen, hydroxyl, carboxyl, carboxylalkyl, oxyacyl, oxyacylamino, thiol, thioalkoxy, substituted thioalkoxy, aryl, heteroaryl, heterocyclic, aryloxy, thioaryloxy, heteroaryloxy, thioheteroaryloxy, nitro, and mono- and di-alkylamino, mono- and di-(substituted alkyl)amino, mono- and di-arylamino, mono- and di-heteroarylamino, mono- and di-heterocyclic amino, and unsymmetric di-substituted amines having different substituents selected from alkyl, substituted alkyl, aryl, heteroaryl, and heterocyclic.

The term "aryl" refers to an unsaturated aromatic carbocyclic group, preferably of from 6 to 14 carbon atoms, having a single ring (e.g., phenyl) or multiple condensed rings (e.g., naphthyl or anthryl), preferably having from 1 to 3 rings. Preferred aryls include phenyl, naphthyl, and the like. Unless otherwise constrained by the definition for the aryl substituent, such aryl groups can optionally be substituted with from 1 to 3 substituents selected from the group consisting of hydroxy, acyl, alkyl, alkoxy, alkenyl, alkynyl, substituted alkyl, substituted alkoxy, substituted alkenyl, substituted alkynyl, amino, aminoacyl, aminocarboxy esters, alkaryl, aryl, aryloxy, carboxyl, carboxylalkyl, acylamino, cyano, halo, nitro, heteroaryl, heterocyclic, oxyacyl, oxyacylamino, thioalkoxy, substituted thioalkoxy, trihalomethyl, mono- and di-alkylamino, mono- and di-(substituted alkyl)amino, mono- and di-arylamino, mono- and di-heteroarylamino, mono- and di-heterocyclic amino, and unsymmetric di-substituted amines having different substituents selected from alkyl, substituted alkyl, aryl, heteroaryl, heterocyclic, and the like. Preferred substituents include alkyl, alkoxy, halo, cyano, nitro, trihalomethyl, and thioalkoxy.

The term "alkaryl" refers to an aryl group with an alkyl substitution. Generally, alkaryl groups herein contain from 6 to 30 carbon atoms. The term "aralkyl" refers to alkylene-aryl groups preferably having from 1 to 10 carbon atoms in the alkylene moiety and from 6 to 10 carbon atoms in the aryl moiety. Such alkaryl groups are exemplified by benzyl, phenethyl, and the like.

The term "acyl" refers to a functional group derived from an oxoacid having one or more hydroxyl groups removed. An acyl group contains a double bonded oxygen atom and an alkyl group. The number of carbons in acyl may be specified. For example, "$C_n$-acyl" refers to a radical having a single carbon atom of a carbonyl group as the point of attachment, further having a linear or branched, cyclic or acyclic structure, further having a total of n carbons, 1 or more hydrogen atoms, and a total of one oxygen atom.

The term "aryloxy" means an aryl group singular bonded to oxygen. A non-limiting example of an aryloxy group is phenoxy, $C_6H_5O$—.

The term "alkoxy" means an alkyl group singular bonded to oxygen.

The term "ether" refers to a compound having and R—O—R' group, where R and R' are each independently alkyl or aryl groups.

The term "solvate" refers to a pharmaceutically acceptable solid form of a specified compound containing solvent molecules as part of the crystal structure. A solvate typically retains at least some of the biological effectiveness of such compound. Solvates can have different solubilities, hygroscopicities, stabilities, and other properties. Examples of solvates include, but are not limited to, compounds in combination with water, isopropanol, ethanol, methanol, DMSO, ethyl acetate, acetic acid, or ethanolamine Solvates are sometimes termed "pseudopolymorphs."

The term "hydrate" refers to a solvate with water.

The term "racemate" refers to a mixture that contains an equal amount of enantiomers.

The term "polymorph" means a crystalline form of a substance that is distinct from another crystalline form of the substance but that shares the same chemical formula.

The term "prodrug" refers to a precursor or derivative of a particular compound which, when consumed, generates the pharmacologically active compound by action of natural processes or biological conditions. For example, a prodrug can be cleaved, hydrolyzed, or oxidized by enzymes in vivo to produce the pharmacologically active compound.

It will be appreciated by one of ordinary skill in the art that asymmetric centers may exist in any of the compounds disclosed herein. Thus, the compounds and pharmaceutical compositions thereof may be in the form of an individual enantiomer, diastereomer, or geometric isomer, or may be in the form of a mixture of stereoisomers. In certain embodiments, the compounds herein are enantiopure compounds. In certain other embodiments, mixtures of stereoisomers or diastereomers are provided. Additionally, the compounds encompass both (Z) and (E) double bond isomers (or cis and trans isomers) unless otherwise specifically designated. Thus, compounds generally depicted in structures herein encompass those structures in which double bonds are (Z) or (E).

It will be appreciated that any of the compounds described herein may be substituted with any number of substituents or functional moieties. In general, the term "substituted" whether preceded by the term "optionally" or not, and substituents contained in formulas, refer to the replacement of hydrogen atoms in a given structure with a specified substituent. When more than one position in any given structure may be substituted with more than one substituent selected from a specified group, the substituent may be either the same or different at every position.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents or organic compounds. For purposes of explanation herein, heteroatoms such as nitrogen may have hydrogen substituents and/or any permissible substituents of organic compounds described herein which satisfy the valencies of the heteroatoms. Furthermore, there is not any intention to be limited in any manner by the permissible substituents of organic compounds. Combinations of substituents and variables envisioned are preferably those that result in the formation of stable compounds useful in the treatment, for example, of infections.

The term "stable" as used herein refers to compounds which possess stability sufficient to allow manufacture and which maintain the integrity of the compound for a sufficient period of time to be detected and preferably for a sufficient period of time to be useful for the purposes detailed herein.

The term "therapeutically effective amount" as used herein means that amount of active compound or pharmaceutical agent that elicits the biological or medicinal response in a tissue system, animal, or human that is being sought by a researcher, veterinarian, medical doctor, or other clinician, which includes alleviation of the symptoms of the disease or disorder being treated.

The term "pharmaceutically acceptable salt" means a salt of a compound. Suitable pharmaceutically acceptable salts of the compounds include acid addition salts which may, for example, be formed by mixing a solution of the compound with a solution of a pharmaceutically acceptable acid.

The term "pharmaceutically acceptable carrier" means a medium that is used to prepare a desired dosage form of the compound. A pharmaceutically acceptable carrier includes solvents, diluents, or other liquid vehicles; dispersion or suspension aids; surface active agents; isotonic agents; thickening or emulsifying agents; preservatives; solid binders; lubricants; and the like.

The abbreviation "NMR" refers to nuclear magnetic resonance. The abbreviation "SAR" refers to structure-activity relationship. The abbreviation "TLC" refers to thin layer chromatography. The term "AdoMet" refers to S-adenosyl-L-methionine. The term "ASA" refers to aspartate semialdehyde. The term "DCM" refers to dichloromethane. The term "FBDD" refers to fragment-based drug discovery. The term "HEPES" refers to 2-[4-(2-hydroxyethyl)piperazin-1-yl]ethane-sulfonic acid. The term "NBS" refers to N-bromosuccinimide. The term "spASADH" refers to *Streptococcus pneumoniae* aspartate semialdehyde dehydrogenase. The term "vcASADH" refers to *Vibrio cholerae* aspartate semialdehyde dehydrogenase. The term "PDB" stands for Protein Data Bank. The term "ANAT" refers to aspartate N-acetyltransferase. The term "NAA" refers to N-acetyl-L-aspartate.

General Description

The aspartate biosynthestic pathway is unique to microbial organisms, with no mammalian homolog. That is, the aspartate pathway is absent in mammals. The products of the aspartate pathway are essential for a wide range of microbial functions, and the genes that code for several of the enzymes in the aspartate pathway are essential for microbial survival. The enzymes that catalyze the reactions in this pathway in infectious organisms are, until now, untested targets for drug intervention. In accordance with one aspect of the present disclosure, these core enzymes are targets for the development of antibiotic compounds, and selective inhibitors of these core enzymes are classes of antimicrobials that are advantageously effective against the growing threat from multidrug resistant infectious organisms.

One aspect of the present disclosure describes inhibitors of aspartate semialdehyde dehydrogenase (ASADH), which is the second enzyme, and a key enzyme, in the aspartate biosynthetic pathway. ASADH lies at the first branch point in the aspartate metabolic pathway (FIG. 1), which leads to the biosynthesis of several essential amino acids and important metabolites. Structure-guided development of these inhibitor compounds has produced low micromolar inhibitors of the target enzyme, with high selectivity observed between the Gram-negative and Gram-positive orthologs of ASADH. Fragment-based drug discovery, modeling, kinetic studies, structure activity relationship studies, and crystal structure studies have been used to synthesize a family of inhibitor compounds. This family of inhibitor compounds includes the most potent inhibitors that have been identified against ASADH. All of the ASADH inhibitors that have been previously identified show only modest affinity against these target enzymes.

The crystal structures of several ASADH enzymes have been determined from Gram-positive and Gram-negative bacteria and fungi. These enzymes share the same substrate binding and active site catalytic groups. However, these enzymes show different inhibition patterns when screened against a low molecular weight small molecule fragments library.

Without wishing to be bound by theory, it is believed that the aspartate pathway in microorganisms and plants controls one-quarter of de novo amino acid biosynthesis. ASADH, coded by the asd gene, catalyzes the production of aspartate semialdehyde (ASA), which is located at a critical junction in this pathway. Genetic studies have revealed that the deletion of the asd gene is fatal to microbes, with genetically-modified bacterial strains lacking the asd gene being no longer viable. In addition to these essential amino acids, a variety of important metabolites that are required for microbial growth and survival are also produced by the aspartate pathway. Methylation reactions, which are crucial for the cell growth and viability, are mediated by S-adenosyl methionine (AdoMet), one of the key products of this pathway. Additionally, 4,5-dihydroxy-2,3-pentanedione and acyl homoserine lactones produced from this pathway have essential roles in bacterial quorum sensing. The expression of a large number of bacterial genes is controlled by these quorum sensing molecules, including those that produce virulence factors such as secreted toxins, proteases, and hemolysins that cause disease pathology. Furthermore, this pathway furnishes components required for the assembly of the polysaccharide matrix of biofilms to protect microbes against phagocytes and antibiotics. Because these many microbial events are controlled by the aspartate pathway, blockage is fatal to microorganisms. The identification of effective inhibitors against this key enzyme provides compounds for the development of new biocides with unique mechanisms of action. In addition, the selective inhibition of different ASADHs can further delay the development of drug resistance by enabling species-specific biocides.

The ASADH inhibitor compounds disclosed herein have the general formula of Formula I:

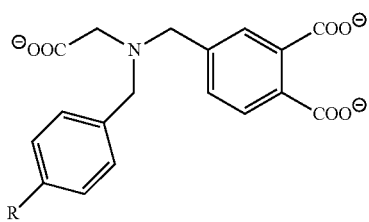

Formula I where R is hydrophobic. Suitable R groups include, but are not limited to, hydrogen, a straight or branched alkane having from 1 to 6 carbons, a halogen, a halogenated alkane having from 1 to 6 carbons, a halogenated alkoxy, or a substituted or unsubstituted cyclic alkane. In some embodiments, R is H, 4-bromo, 4-methyl, 4-trifluoromethyl, 4-trifluoromethoxy, 4-difluoromethoxy, 4-tert-butyl, 4-(2-perfluoropropyl), 4-phenyl, 4-((2-benzyl)vinyl), or 4-trifluoromethyl. Non-limiting examples of the ASADH inhibitor compounds described herein include N-carboxymethyl-3,4-dicarboxybenzylamine; N-carboxyethyl-3,4-dicarboxybenzylamine; N-((2-methyl)carboxymethyl)-3,4-dicarboxybenzylamine; N-((2-hydroxymethyl)carboxymethyl)-3,4-dicarboxybenzylamine; N-methyl, N-carboxymethyl-2,3-dicarboxybenzylamine; N-methyl, N-carboxymethyl-3,4-dicarboxybenzylamine; N-allyl, N-carboxymethyl-3,4-dicarboxybenzylamine; N-acetonitrile, N-carboxymethyl-3,4-dicarboxybenzylamine; N-benzyl, N-carboxymethyl-3,4-dicarboxybenzylamine; N-(1-naphthyl)-N-carboxymethyl-3,4-dicarboxybenzylamine; N-(2-naphthyl)-N-carboxymethyl-3,4-dicarboxybenzylamine; N-(ethylmorpholino)-N-carboxymethyl-3,4-dicarboxybenzylamine; N-(4-biphenyl)-N-carboxymethyl-3,4-dicarboxybenzylamine; N-(2-bromobenzyl)-N-carboxymethyl-3,4-dicarboxybenzylamine; N-(3-bromobenzyl)-N-carboxymethyl-3,4-dicarboxybenzylamine; N-(4-bromobenzyl)-N-carboxymethyl-3,4-dicarboxybenzylamine; N-(2-methylbenzyl)-N-carboxymethyl-3,4-dicarboxybenzylamine; N-(3-methylbenzyl)-N-carboxymethyl-3,4-dicarboxybenzylamine, N-(4-methylbenzyl)-N-carboxymethyl-3,4-dicarboxybenzylamine; N-(2-trifluoromethylbenzyl)-N-carboxymethyl-3,4-dicarboxybenzylamine; N-(3-trifluoromethylbenzyl)-N-carboxymethyl-3,4-dicarboxybenzylamine; N-(4-trifluoromethylbenzyl)-N-carboxymethyl-3,4-dicarboxybenzylamine; N-(2-trifluoromethyoxybenzyl)-N-carboxymethyl-3,4-dicarboxybenzylamine; N-(3-trifluoromethoxybenzyl)-N-carboxymethyl-3,4-dicarboxybenzylamine; N-(4-trifluoromethoxybenzyl)-N-carboxymethyl-3,4-dicarboxybenzylamine; N-(4-difluoromethoxybenzyl)-N-carboxymethyl-3,4-dicarboxybenzylamine; N-(4-carboxybenzyl)-N-carboxymethyl-3,4-dicarboxybenzylamine; N-(4-carboxamidebenzyl)-N-carboxymethyl-3,4-dicarboxybenzylamine; N-(4-t-butylbenzyl)-N-carboxymethyl-3,4-dicarboxybenzylamine; N-(4-(2-perfluoropropyl))-N-carboxymethyl-3,4-dicarboxybenzylamine; N-(4-bromobenzyl)-N-carboxyethyl-3,4-dicarboxybenzylamine; N-(4-trifluoromethylbenzyl)-N-carboxymethyl-3,4-dicarboxybenzylamine; and N-acetal-N-carboxymethyl-3,4-dicarboxybenzylamine.

Formula I is shown in a trianionic form, which, without wishing to be bound by theory, is believed to be the active form of the ASADH inhibitors. Salts of the compounds, such as a sodium salts, and esters of the compounds, such as methyl esters, are explicitly included herein. Other salts and esters include, but are not limited to, pharmaceutically acceptable alkali salts, such as lithium salts or potassium salts, and pharmaceutically acceptable alkyl esters, such as ethyl esters. Furthermore, it is understood that salts and esters include mixed salts and esters, for example where one or two of the anionic sites are ionically bonded to a cation(s) and the remaining one or two anionic sites form esters.

In accordance with another aspect of the present disclosure, N-derivatives of phthalate have been designed and tested as potent inhibitors of aspartate N-acetyltransferase (ANAT), which is the brain enzyme responsible for the synthesis of N-acetylaspartate (NAA). Dramatically elevated NAA levels are one of the underlying causes of a fatal neurological diseased called Canavan disease. Inhibition of ANAT can lower NAA levels in these patients and serve as a treatment option for this currently uncurable and untreatable disease.

Canavan disease (CD) is a fatal, neurological disease that is caused by an interruption in the metabolism of NAA, a critical amino acid. Defects at multiple locations in the aspA gene that codes for aspartoacylase lead to mutant forms of this enzyme that are either not expressed or rapidly degraded, or have significantly impaired catalytic activity. As a consequence, the substrate NAA accumulates to unusually elevated levels, and the products of this reaction, aspartic acid and acetate, are not made in oligodendrocytes. Various hypotheses of the molecular basis for CD have been proposed and tested, including toxic accumulation of NAA, increased NAAG neurotransmitter production, osmotic effects of NAA accumulation, and defects in fatty acid biosynthesis as a consequence of acetate deficiency Animal models in which the aspA gene had been knocked out were found to reproduce many of the disease symptoms. Unexpectedly, a second gene knock-out introduced in the Nat8l gene, which codes for the enzyme that synthesizes NAA, reverse these adverse effects, leading to normal myelination and a decrease in CD symptoms. These results place an increased importance on the activity of aspartate N-acetyltransferase (ANAT), the brain enzyme that catalyzes the synthesis of NAA.

Identifying and developing effective enzyme inhibitors requires the availability of a selective enzyme activity assay and the isolation and purification of the target enzyme. A fixed-time ANAT assay using radiolabeled NAA has been developed, but the membrane-associated nature of ANAT makes enzyme purification a significant challenge. ANAT is difficult to purify. Nonetheless, in order to test the ANAT inhibitory activity of any compounds, a stable, soluble, and active form of the enzyme ANAT has to be produced. This can be accomplished, for example, as described in U.S. Provisional Patent Application No. 62/216,700, which is incorporated herein by reference for all purposes. Specifically, fusion constructs with solubilizing protein partners have been used to obtain an active and soluble form of aspartate N-acetyltransferase, as described in U.S. Provisional Patent Application No. 62/216,700. ANAT has been found to be highly selective for L-aspartate as the acetyl group acceptor. The introduction of a methyl group at carbon-3 or the incorporation of a second amino group are each tolerated, but the extension of the dioic acid structure by one carbon (glutamate vs. aspartate) causes a drop in catalytic efficiency to less than 1% that of the physiological substrate.

Phthalate derivatives have been synthesized and tested for inhibition against ANAT using the fusion constructs described above, yielding a series of potent ANAT inhibitors. The ANAT inhibitors can be used to treat, prevent, or ameliorate Canavan disease in a subject in need thereof. The ANAT inhibitors can also be used to reduce ANAT activity in a cell, such as a brain cell.

In some embodiments, ANAT inhibitors have the general formula of Formula II:

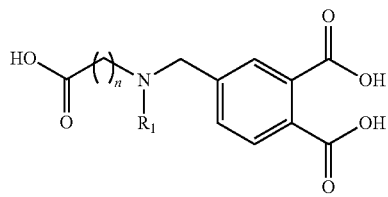

Formula II where n is either 1 or 2, and $R_1$ is substituted or unsubstituted aryl, alkyl, aralkyl, or aryloxy. Example $R_1$ groups include, but are not limited to, napthyl, biphenyl, allyl, benzyl, halo-substituted benzyl, alkylbenzyl, and carboxybenzyl. Two non-limiting examples Formula II compounds are those having a 1-naphthyl $R_1$ group, where n is either 1 or 2.

In some embodiments, the ANAT inhibitors have the general formula of Formula III:

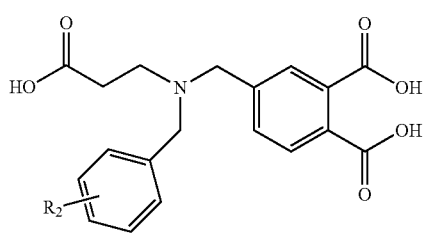

Formula III where $R_2$ is a halogen or substituted or unsubtitued aryl, alkyl, or carboxyl. The $R_2$ substituent can be present in any of the ortho, meta, or para positions. When $R_2$ is aryl, the aryl group can form a fused bicyclic ring. Example $R_2$ groups include, but are not limited to: methyl, bromo, trifluoromethyl, difluoromethyl, tert-butyl, 2-perfluoropropyl, carboxy, carboxamide, acetyl, and carboxy-1-napthyl.

One non-limiting example of an ANAT inhibitor is compound (50):

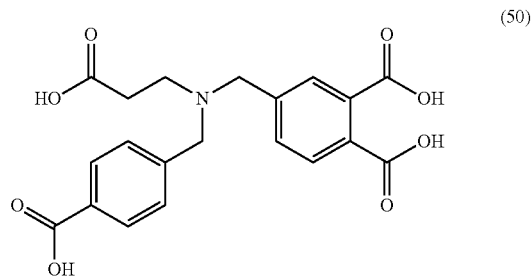 [SMILES: O=C(O)CCN(Cc1ccc(C(=O)O)cc1)Cc1ccc(C(=O)O)c(C(=O)O)c1]

(50)

Another non-limiting example of an ANAT inhibitor is compound (49):

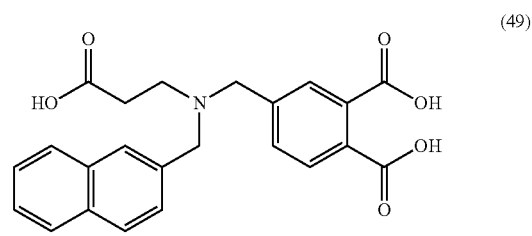 [SMILES: O=C(O)CCN(Cc1ccc(C(=O)O)c(C(=O)O)c1)Cc1ccc2ccccc2c1]

(49)

Another non-limiting example of an ANAT inhibitor is compound (41):

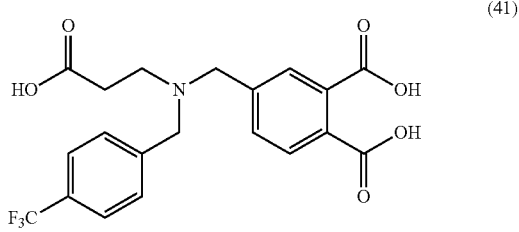 [SMILES: O=C(O)CCN(Cc1ccc(C(F)(F)F)cc1)Cc1ccc(C(=O)O)c(C(=O)O)c1]

(41)

Another non-limiting example of an ANAT inhibitor is compound (54):

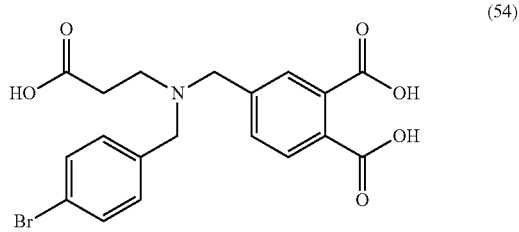 [SMILES: O=C(O)CCN(Cc1ccc(Br)cc1)Cc1ccc(C(=O)O)c(C(=O)O)c1]

(54)

Another non-limiting example of an ANAT inhibitor is compound (40):

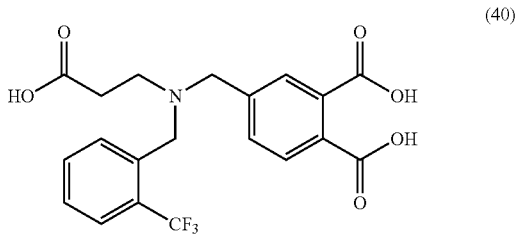 [SMILES: O=C(O)CCN(Cc1ccc(C(=O)O)c(C(=O)O)c1)Cc1ccccc1C(F)(F)F]

(40)

Another non-limiting example of an ANAT inhibitor is compound (53):

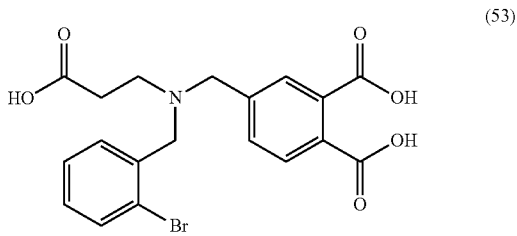 [SMILES: O=C(O)CCN(Cc1ccc(C(=O)O)c(C(=O)O)c1)Cc1ccccc1Br]

(53)

Methods of Making

Non-limiting examples of methods of making the ASADH inhibitor compounds, and the ANAT inhibitor compounds, described herein are shown schematically in FIGS. 2-6 and FIGS. 8-9. As seen from these schemes, one non-limiting method of making a phthalate ASADH or ANAT inhibitor compound begins with a dicarboxylic methylphthalate, which is esterified, such as by reaction with methanol, to produce a methylphthalate dimethyl ester. The methylphthalate dimethyl ester can be bromonated, such as by reacting it with N-bromosuccinimide (NBS), to produce a bromomethylphthalate dimethyl ester.

In one embodiment, the bromomethylphthalate dimethyl ester is coupled with glycine methyl ester to produce an esterified N-carboxymethyl dicarboxybenzylamine. In another embodiment, the bromomethylphthalate dimethyl ester is coupled with β-alanine methyl ester to produce an esterified N-carboxyethyl dicarboxybenzylamine. In either case, the methyl groups can then be replaced by a suitable cation via hydrolysis in the presence of a base, such as NaOH, to produce either an N-carboxymethyl dicarboxybenzylamine or an N-carboxyethyl dicarboxybenzylamine.

In other embodiments, the bromomethylphthalate dimethyl ester is reacted with an alkyl halide or benzyl halide, for instance in the presence of $NaHCO_3$, to produce a corresponding N-derivatized benzylamine ester. The N-derivatized benzylamine esters can be base-hydrolyzed to produce corresponding salts, such as sodium salts, of the N-derivatized benzylamines.

In other embodiments, a methylphthalate dimethyl ester can be reacted with an alkyl halide or benzyl halide to produce a corresponding N-derivatized alkyl or benzyl amine. This process is depicted schematically in Tables 4-5 (FIGS. 8-9) for the production of phthalate ANAT inhibitor compounds.

It is understood that other methods of making the ASADH inhibitor or ANAT inhibitor compounds described herein are encompassed within the present disclosure.

Prodrugs

Any of the ASADH inhibitors or ANAT inhibitors described herein can be formulated or administered as prodrugs. As one non-limiting example, the compounds can be administered as methyl esters instead of salts, where the carboxylates are protected by methyl groups instead of being bound to metallic cations. Bacteria have methyl esterases that cleave methyl esters. Therefore, once a methyl ester-containing ASADH inhibitor is inside a bacterial cell, the methyl groups are cleaved, which results in exposed $COO^-$ groups. Without wishing to be bound by theory, it is believed that the $COO^-$ groups are important for binding to the ASADH target. Thus, the exposure of these carboxylates activates the ASADH inhibitors inside the bacterial cells. However, other prodrug forms of the ASADH inhibitor compounds and the ANAT inhibitor compounds are also encompassed within the present disclosure.

Pharmaceutical Compositions

Pharmaceutical compositions of the present disclosure comprise an effective amount of a phthalate inhibitor (i.e., an ASADH inhibitor compound, an ANAT inhibitor compound, or a prodrug of either the aforementioned), and/or additional agents, dissolved or dispersed in a pharmaceutically acceptable carrier. The phrases "pharmaceutical" or "pharmacologically acceptable" refer to molecular entities and compositions that produce no adverse, allergic, or other untoward reaction when administered to an animal, such as, for example, a human. The preparation of a pharmaceutical composition that contains at least one compound or additional active ingredient will be known to those of skill in the art in light of the present disclosure, as exemplified by Remington's Pharmaceutical Sciences, 2003, incorporated herein by reference. Moreover, for animal (e.g., human) administration, it is understood that preparations should meet sterility, pyrogenicity, general safety, and purity standards as required by FDA Office of Biological Standards.

A composition disclosed herein may comprise different types of carriers depending on whether it is to be administered in solid, liquid or aerosol form, and whether it need to be sterile for such routes of administration as injection. Compositions disclosed herein can be administered intravenously, intradermally, transdermally, intrathecally, intraarterially, intraperitoneally, intranasally, intravaginally, intrarectally, intraosseously, periprosthetically, topically, intramuscularly, subcutaneously, mucosally, intraosseosly, periprosthetically, in utero, orally, topically, locally, via inhalation (e.g., aerosol inhalation), by injection, by infusion, by continuous infusion, by localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 2003, incorporated herein by reference).

The actual dosage amount of a composition disclosed herein administered to an animal or human patient can be determined by physical and physiological factors such as body weight, severity of condition, the type of disease being treated, previous or concurrent therapeutic interventions, idiopathy of the patient, and the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, an active compound may comprise between about 2% to about 75% of the weight of the unit, or between about 25% to about 60%, for example, and any range derivable therein. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In certain embodiments, a composition herein and/or additional agent is formulated to be administered via an alimentary route Alimentary routes include all possible routes of administration in which the composition is in direct contact with the alimentary tract. Specifically, the pharmaceutical compositions disclosed herein may be administered orally, buccally, rectally, or sublingually. As such, these compositions may be formulated with an inert diluent or with an assimilable edible carrier, or they may be enclosed in hard- or soft-shell gelatin capsules, they may be compressed into tablets, or they may be incorporated directly with the food of the diet.

In further embodiments, a composition described herein may be administered via a parenteral route. As used herein, the term "parenteral" includes routes that bypass the alimentary tract. Specifically, the pharmaceutical compositions disclosed herein may be administered, for example but not limited to, intravenously, intradermally, intramuscularly, intraarterially, intrathecally, subcutaneous, or intraperitoneally (U.S. Pat. Nos. 6,753,514; 6,613,308; 5,466,468; 5,543,158; 5,641,515; and 5,399,363 are each specifically incorporated herein by reference in their entirety).

Solutions of the compositions disclosed herein as free bases or pharmacologically acceptable salts may be prepared in water suitably mixed with a surfactant, such as hydroxypropylcellulose. Dispersions may also be prepared in glycerol, liquid polyethylene glycols, and mixtures thereof, and in oils. Under ordinary conditions of storage and use, these preparations may contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In some cases, the form must be sterile and must be fluid to the extent that easy injectability exists. It should be stable under the conditions of manufacture and storage and should be preserved against the contaminating action of microorganisms, such as bacteria and fungi. The carrier can be a solvent or dispersion medium containing, for example, water, ethanol, polyol (i.e., glycerol, propylene glycol, liquid polyethylene glycol, and the like), suitable mixtures thereof, and/or vegetable oils. Proper fluidity may be maintained, for example, by the use of a coating, such as lecithin, by the maintenance of the required particle size in the case of dispersion, and/or by the use of surfactants. The prevention of the action of microorganisms can be brought about by various antibacterial and antifungal agents, such as, but not limited to, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption such as, for example, aluminum monostearate or gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in 1 mL of isotonic NaCl solution and either added to 1000 mL of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

Sterile injectable solutions are prepared by incorporating the compositions in the required amount in the appropriate solvent with various other ingredients enumerated above, as required, followed by filtered sterilization. Generally, dispersions are prepared by incorporating the various sterilized compositions into a sterile vehicle which contains the basic dispersion medium and the required other ingredients from those enumerated above. In the case of sterile powders for the preparation of sterile injectable solutions, some methods of preparation are vacuum-drying and freeze-drying techniques which yield a powder of the active ingredient plus any additional desired ingredient from a previously sterile-filtered solution thereof. A powdered composition is combined with a liquid carrier such as, but not limited to, water or a saline solution, with or without a stabilizing agent.

In other embodiments, the compositions may be formulated for administration via various miscellaneous routes, for example, topical (i.e., transdermal) administration, mucosal administration (intranasal, vaginal, etc.) and/or via inhalation.

Pharmaceutical compositions for topical administration may include the compositions formulated for a medicated application such as an ointment, paste, cream, or powder. Ointments include all oleaginous, adsorption, emulsion, and water-soluble based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones, and luarocapram. Possible bases for compositions for topical application include polyethylene glycol, lanolin, cold cream, and petrolatum, as well as any other suitable absorption, emulsion, or water-soluble ointment base. Topical preparations may also include emulsifiers, gelling agents, and antimicrobial preservatives as necessary to preserve the composition and provide for a homogenous mixture. Transdermal administration of the compositions may also comprise the use of a "patch." For example, the patch may supply one or more compositions at a predetermined rate and in a continuous manner over a fixed period of time.

In certain embodiments, the compositions may be delivered by eye drops, intranasal sprays, inhalation, and/or other aerosol delivery vehicles. Methods for delivering compositions directly to the lungs via nasal aerosol sprays has been described in U.S. Pat. Nos. 5,756,353 and 5,804,212 (each specifically incorporated herein by reference in their entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts and could be employed to deliver the compositions described herein. Likewise, transmucosal drug delivery in the form of a polytetrafluoroetheylene support matrix is described in U.S. Pat. No. 5,780,045 (specifically incorporated herein by reference in its entirety), and could be employed to deliver the compositions described herein.

It is further envisioned the compositions disclosed herein may be delivered via an aerosol. The term aerosol refers to a colloidal system of finely divided solid or liquid particles dispersed in a liquefied or pressurized gas propellant. The typical aerosol for inhalation consists of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age, weight, and the severity and response of the symptoms.

In particular embodiments, the compounds and compositions described herein are useful for treating various infections such as, but not limited to, bacterial infections, viral infections, fungal infections, and protozoal infections. The compounds are particularly useful for the treatment of infection in patients infected with a multidrug-resistant pathogen. Such pathogens include, but are not limited to, *Streptococcus pneumoniae*, drug-resistant *Campylobacter*, drug-resistant *Neisseria gonorrhoeae*, drug-resistant nontyphoidal *Salmonella*, methicillin-resistant *Staphylococcus aureus* (MRSA), drug-resistant *Shigella*, extended-spectrum β-lactamase (ESBL)-producing Enterobacteriaceae, vancomycin-resistant *Enterococcus* (VRE), carbapenem-resistant Enterobacteriaceae (CRE), and *Clostridium difficile*.

In particular embodiments, the compounds and compositions described herein are useful for treating, preventing, or ameliorating Canavan disease. In particular embodiments, the compounds and compositions described herein are useful for inhibiting ANAT activity in a cell, such as a brain cell.

In particular embodiments, the compounds and compositions described herein are useful for both treating various infections and treating, preventing, or ameliorating Canavan disease.

Furthermore, the compounds and compositions herein can be used in combination therapies. That is, the compounds and compositions can be administered concurrently with, prior to, or subsequent to one or more other desired therapeutic or medical procedures or drugs. The particular combination of therapies and procedures in the combination regimen will take into account compatibility of the therapies and/or procedures and the desired therapeutic effect to be achieved. Combination therapies include sequential, simultaneous, and separate administration of the active compound in a way that the therapeutic effects of the first administered procedure or drug is not entirely disappeared when the subsequent procedure or drug is administered.

By way of a non-limiting example of a combination therapy, a compound or composition herein can be administered in combination with one or more suitable anti-infective agents including, but not limited to: antibiotics, antibacterials, antifungals, antivirals, and antiprotozoals. In certain embodiments, the anti-infective agent is one or more of: macrolide antibiotics, such as clarithromycin, erythromycin, or azithromycin; anthracycline antibiotics, such as doxorubicm or daunorubicin; camptothecin or its analogs, such as topotecan and irenotecan; quinolone antibiotics, such as ciprofloxacin, ofloxacin, levofloxacin, clinafloxacin, or moxifloxacin; cephalosporins, such as cefotaxime, ceftriaxone, ceftazidime, or cefepime; β-lactam antibiotics, such as cefotetan, or aztreonam; penicillins, such as amoxicillin, or piperacillin; aminoglycosides, such as streptomycin; sulfonamides, such as trimethoprim/sulfamethoxazole; carbapenems; bacitracin; gramicidin; mupirocin; chloramphenicol; thiamphenicol; fusidate sodium; lincomycin; clindamycin; novobiocin; polymyxins; rifamycins; spectinomycin; tetracyclines; vancomycin; teicoplanin; streptogramins; anti-folate agents, including trimethoprim and its combinations, and pyrimethamine; synthetic antibacterials, such as nitrofurans, methenamine mandelate, or methenamine hippurate; nitroimidazoles; fluoroquinolones; isoniazid; ethambutol; pyrazinamide; para-aminosalicylic acid (PAS); cycloserine; capreomycin; ethionamide; prothionamide; thiacetazone; viomycin; amikacin; netilmicin; fosfomycin; gentamicin; teicoplanin; ampicillin sodium/sulbactam sodium (marketed under the brand name Unasyn® by Pfizer); ticarcillin disodium/clavulanate potassium (marketed under the brand name Timentin® by GlaxoSmithKline); quinupristin/dalfopristin (marketed under the brand name Synercid® by Aventis); piperacillin sodium/tazobactam sodium (marketed under the brand name Zosyn® by Lederle Pharmaceutical); imipenem/cilastatin (marketed under the brand name Primaxin® by Merck); antivirals, such as ganciclovir, oseltamivir, acyclovir, rimantadine, abacavir, adefovir, amantadine, amprenavir, atazanavir, capravirine, delavirdine, didanosine, efavirenz, emivirin, emtricitabine, enfurvirtide, fosamprenavir, idoxuridine, indinavir, lamivudine, lopinavir, memantine, mozenavir, nelfinavir, oseltamivir, pentafuside, ritonavir, saquinavir, stavudine, tenofovir, tipranavir, zalcitabine, zanamivir, or zidovudine; anti-fungals, such as Amphotericin B, fluconazole, ltraconazole, liposomal amphotericin, posaconazole, voriconazole, nystatin, griseofulvin, natamycin, rimocidin, filipin, or candicin; or antiprotozoals, such as elornithine, furazolidone, melarsoprol, metronidazole, ornidazole, paromomycin sulfate, pentamidine, pyrimethamine, or tinidazole.

Kits

It is envisioned that the compounds, compositions, and methods described herein could be embodied as parts of a kit or kits. A non-limiting example of such a kit is a kit for making an ASADH inhibitor compound, which includes a bromomethylphthalate dimethyl ester and either an alkyl halide or a benzyl halide in separate containers, where the containers may or may not be present in a combined configuration. Another non-limiting example of such a kit is a kit for making an ANAT inhibitor compound, which includes a methylphthalate dimethyl ester and an alkyl halide or a benzyl halide in separate containers, where the containers may or may not be present in a combined configuration. Many other kits are possible, such as kits further comprising a pharmaceutically acceptable carrier, diluent, or excipient, or further comprising a suitable anti-infective for a combination therapy with an ASADH inhibitor. The kits may further include instructions for using the components of the kit to practice the subject methods. The instructions for practicing the subject methods are generally recorded on a suitable recording medium. For example, the instructions may be present in the kits as a package insert or in the labeling of the container of the kit or components thereof. In other embodiments, the instructions are present as an electronic storage data file present on a suitable computer readable storage medium, such as a flash drive, CD-ROM, or diskette. In other embodiments, the actual instructions are not present in the kit, but means for obtaining the instructions from a remote source, such as via the internet, are provided. An example of this embodiment is a kit that includes a web address where the instructions can be viewed and/or from which the instructions can be downloaded. As with the instructions, this means for obtaining the instructions is recorded on a suitable substrate.

EXAMPLES

Example I—ASADH Inhibitors

In this Example, the structure-activity properties of ASADH inhibitors were examined, and a systematic approach to develop compounds that inhibit the bacterial orthologs of ASADH with enhanced selectivity and with significantly greater affinity than previously observed, by elaborating the phthalate core structure, is described. Structure-guided development of the ASADH inhibitors has produced low micro-molar inhibitors of the target enzyme with selectivity observed between the Gram-negative and Gram-positive orthologs of ASADH. Significant improvements in binding affinities, approaching three-orders of magnitude, and dramatically enhanced ortholog selectivity have now been achieved for certain substituted N-benzyl derivatives, with the highest affinities driven by the incorporation of hydrophobic para-substituents on the introduced benzyl ring. Initial inhibitors showed low-millimolar $K_i$ values, but had good ligand-binding efficiencies on the order of 0.2-0.3 kcal/mole/heavy atom. Some surprising changes in the orientation of the bound inhibitors limited the optimal affinity that could be achieved. However, modification at the amine position led to a 1000-fold increase in affinity. The best inhibitors also have a 70-fold selectivity between bacterial enzymes. The most effective ASADH inhibitor compounds inhibited the ASADH from S. pneumonia with enhanced selectivity and with significantly greater affinity than previously observed. (FIGS. 4-5, Tables 1-2.)

To produce ASADH inhibitor compounds, the carboxylates of commercially available 4-methylphthalic acid (1) were protected by esterification (1Me), followed by free radical bromination (2Me). Coupling to either 2-aminoacetate methyl ester or 3-aminopropionate methyl ester by nucleophilic displacement of the introduced bromine, followed by base-catalyzed hydrolysis, yielded the corresponding amine-containing 4-(carboxymethylaminomethyl) and 4-(2-carboxyethylaminomethyl) phthalate analogs 3 and 4, respectively. (FIGS. 2A-2B, Schemes 1A-1B.) The affinities of these parent compounds for representative Gram-negative (Vibrio cholerae) and Gram-positive (Streptococcus pneumoniae) forms of ASADH were examined, and then improved through the production of an extensive series of derivatives at the introduced secondary amine.

Compound 4, with the longer N-carboxyethyl side chain, did not show appreciable inhibition of vcASADH, but does inhibit spASADH a relatively weak $K_i$ of 2.4 mM. These values are comparable to those that were observed for the inhibition by 3-(3-carboxypropyl)phthalate despite the longer side chain, the introduction of a nitrogen heteroatom, and the shift of the side chain from the 3- to the 4-position. The one-carbon shorter homolog (3) shows some improvement, functioning as a 0.5 mM inhibitor of vcASADH and a two-fold stronger inhibitor of spASADH (FIG. 4, Table 1).

Attempts to synthesize the corresponding 3-position analogs to compounds 3 and 4 were thwarted by cyclization between the side chain amine nitrogen and the 2-carboxyl group. Blocking the nitrogen by methylation did allow completion of this synthesis (FIG. 3, Scheme 2), but this compound (9) showed only weak inhibition ($K_i$=1.8 mM) of spASADH and no inhibition of vcASADH, comparable to the affinities that were observed with compound 4.

Varying the nature of the N-carboxymethyl side chain through the introduction of an α-L-methyl group (5) or an α-L-hydroxymethyl group (6) had no appreciable effect on the binding affinity to either ASADH ortholog (FIG. 4, Table 1). To explore the improved affinity of the parent compound 3 to the ASADHs, several additional derivatives were synthesized through coupling with various halides at the secondary amine position. However, the introduction of simple alkyl, allyl, nitrile, aryl, or aldehyde groups (10-13, 37) did not alter the inhibitory properties of these compounds (FIG. 4, Table 1). Next, a series of substituted benzyl substituents were introduced at this amine position. Significant changes were then observed in both binding affinity and in binding selectivity between the two forms of ASADH, with the improvement in activity being highly dependent both on the nature and the position of the aromatic substitutions. Coupling with benzyl halides substituted with either bromo (18 and 19) or methyl groups (21 and 22) at the ortho- or meta-positions did not yield any improvement in affinity, but similar substitutions at the para-position of the benzyl ring (20 and 23) resulted in a 10-fold improvement in the $K_i$ values with spASADH (FIG. 5, Table 2). Surprisingly, these para-substituted derivatives did not show any improved affinity for vcASADH.

The effect of changes in the methyl substituent was examined Replacement of the o-methyl or m-methyl groups with either trifluoromethyl (24 and 25) or trifluoromethoxy groups (27 and 28) did not alter the affinity of these derivatives for either spASADH or vcASADH. (FIG. 5, Table 2.) However, replacing the p-methyl group with these same substituents (26 and 29) led to a two-fold additional improvement in binding affinity for spASADH. (FIG. 5, Table 2.) Changing p-trifluoromethoxy (29) to p-difluoromethoxy (30) reversed this improvement, while an additional two-fold improvement ($K_i$=16 μM) was observed for the p-tert-butylbenzyl derivative (33) as an inhibitor of spASADH. (FIG. 5, Table 2.) To further enhance the hydrophobic nature of the p-benzyl substituent, a perfluorinated 2-propyl derivative was prepared (34). This compound shows the most potent inhibition among this family of structures, with a $K_i$ of 9 μM for spASADH and over 70-fold selectivity for this enzyme form relative to the Gram-negative ASADH ortholog from *V. cholerae*. (FIG. 5, Table 2.) As was seen for the parent compounds, for each of these synthesized derivatives no significant changes were observed in their affinity for the Gram-negative vcASADH.

Now that the importance of para-hydrophobic substituents had been established, some additional groups were incorporated in place of the benzyl group to examine the nature of this hydrophobic interaction. Substitution with a naphthyl group coupled at either the 1- or 2-position (14 and 15) resulted in slightly worse inhibition, while the replacement of the benzyl group with a morpholine (16) gave only a slight improvement. The greatest change was observed with the incorporation of a biphenyl group (17), resulting in 25-fold improved inhibition of spASADH relative to the parent benzyl derivative (FIG. 4, Table 1).

The only outlier from this correlation between higher affinity and increased para-hydrophobicity was the observation that the p-carboxylbenzyl derivative (31) has comparable affinity to that observed for the p-methylbenzyl derivative (23). Without wishing to be bound by theory, it is believed that the improved affinity for this charged benzyl derivative is likely due to the orientation of this side chain in a different binding position, perhaps making an electrostatic interaction with a positively-charged amino acid side chain near the active site. To determine whether this is true, the p-carboxyl group was replaced with a polar but uncharged substituent, a carboxamide group (32). This derivative showed a 3-fold loss of affinity to a value that is now comparable to that of the underivatized parent compound (3) (FIG. 5, Table 2).

Now that the significance of these p-substituted benzyl derivatives as potent and selective ASADH inhibitors has been demonstrated, several longer homologs of these derivatives were synthesized starting from parent compound 4 (FIGS. 2A-2B, Schemes 1A-1B) to determine if the improved affinities of these derivatives would be able to overcome the lower affinity of this parent compound. However, in these cases neither the p-bromobenzyl nor the p-trifluoromethylbenzyl derivatives of compound 4 gave better than low millimolar inhibition of spASADH, and no inhibition of vcASADH was observed with these derivatives.

Discussion

The past few decades have seen the attention of the drug development community increasing focusing on disease such as cancer and cardiovascular diseases, as the leading causes of death. However, the development of a diversity of defensive mechanisms by microbes against most of the current antibiotics demands a renewed focus from the scientific community to identify unique and selective pathways that can be targeted for development of new classes of antibiotics. The aspartate pathway, absent in mammals but present in microbes and plants, is a critical and essential pathway that meets these criteria. The present disclosure describes the targeting of aspartate semialdehyde dehydrogenase (ASADH), which controls the first branch point in this pathway, for the design of new, potent, and selectivity inhibitors. Inhibition of ASADH provides the basis for development of selective drugs that can function through a different mechanism of action against this different target.

Fragment library screening against this enzyme target uncovered several non-substrate-like structures that function as modest inhibitors of the ASADHs. Among these compounds were some aromatic inhibitors that offered the possibility of additional structural elaborations. Subsequent molecular modeling and docking studies starting with these core structures led to the identification of aryl di- and trianionic compounds that were determined to be low millimolar inhibitors of both Gram-negative and Gram-positive forms of ASADH. Extending one of the carboxylate side chains into an adjacent anionic binding pocket was explored to improve inhibitor affinity. Unfortunately, some steric clashes coupled with multiple possible binding orientations precluded the development of this core structure into more potent inhibitors. Without wishing to be bound by theory, what was needed to realize the objective of potent inhibition was the introduction of additional functionality that would favor a single orientation when bound to the enzyme.

Some parent aryl dicarboxylate structures have now been synthesized with the inclusion of a secondary amine side chain that can be further elaborated. Attempts were made to directly mimic the 3-(3-carboxypropyl)phthalate structure that shows good binding orientation at the active site of spASADH through the replacement with an aminoethylcarboxylate side chain. This synthetic approach failed because of rapid cyclization between the secondary amine and the carboxyl group at the 2-position. Protection of this amine by the presence of a methyl group did allow synthesis of the desired structure (FIG. 3, Scheme 2) which, unfortunately, was no more potent than the original compound.

Switching the aminoalkylcarboxyl side chain from the 3- to the 4-position on the benzyl ring avoided this cyclization reaction and has led to a much more productive series of ASADH inhibitors. The parent compound 3 is a high millimolar inhibitor of the ASADHs with a 2-fold preference for the Gram-positive spASADH. Exploring the reactivity of the introduced secondary amine through the incorporation of a set of simple substituents did not alter either the affinity or the selectivity relative to the parent compound (FIG. 4, Table 1). However, improved affinity was observed when substituted aryl substituents were introduced at this amine position. Simple o- or m-substituted benzyl groups were slightly poorer inhibitors of spASADH when compared to the benzyl substituent (compound 13), but the corresponding p-substituted benzyl derivatives were substantially more potent spASADH inhibitors and now showed 10-fold selectivity for this enzyme form (FIG. 5, Table 2). The more hydrophobic fluorinated p-methylbenzyl derivatives gave a 2-fold additional improvement in affinity, with slight differences between di- and trifluoromethyl and between methyl and methoxy.

Without wishing to be bound by theory, it is believed that placing a hydrophobic group at the para-position is likely accessing a hydrophobic pocket within the active site of spASADH. Consistent with this belief is the observation that the p-tert-butylbenzyl derivative (compound 33) is the most potent inhibitor in this series and also has over 40-fold selectivity for spASADH (FIG. 5, Table 2). The most hydrophobic para-substituent tested, perfluoroisopropyl (compound 34), was the most potent inhibitor of spASADH, with a low micromolar K value and 70-fold selectivity over the Gram-negative vcASADH. Further elaboration at this position through the introduction of a p-styrene group leads to a substantial loss of activity, presumably due to the additional steric bulk. The only additional aromatic hydrophobic group that allowed improved binding affinity was a p-biphenyl group (17), indicating the presence of a deep but narrow hydrophobic pocket near the active site that is being accessed by this side chain. Modificaitons in the N-carboxylmethyl side chain through the introduction of α-substituents (5 and 6) did not lead to enhanced affinity, and carbon chain homologation (4) caused a substantial affinity loss, even in the presence of the more optimal benzyl derivatives (35 and 36).

A major cause of "off-target" effects with drug candidates is not the lack of affinity for the target of interest, but a lack of specificity that allows additional interactions with unintended targets. Without wishing to be bound by theory, it is believed that there are no close mammalian orthologs of ASADH that would provide competing target proteins. In addition, the most potent of these inhibitors now displays enhanced selectivity against the identical enzyme from another bacterial species. This increases the confidence in the exquisite selectivity of this developed class of ASADH inhibitors.

The original compound in this phthalate series, 3-(3-carboxypropylphthalate), produced via the synthetic route shown in Scheme 3 in FIG. 6, binds in a unique position in the active site of ASADH, base-stacking with the nicotinamide ring of the NADP cofactor while also making electrostatic interactions between the inhibitor carboxylate groups and the side chains of Ser96, Arg99 and Arg245. However, minor structural alterations lead to substantial changes in the bound orientation of these structurally-related inhibitors. Without wishing to be bound by theory, it is believed that this orientational and conformational flexibility is the cause for the much lower measured affinity than would be predicted based on the number of favorable binding interactions observed in the optimally-oriented enzyme-inhibitor structure. Derivatization of the introduced secondary amine through the introduction of para-hydrophobic benzyl substituents makes additional productive binding interactions that constrain these multiple orientations, leading to the realization of potent and selective inhibition of ASADH.

Docking of the most potent inhibitors into the active site of spASADH offers an explanation both for the improved affinity of these derivatives and for the observed ortholog selectivity. Using the structure of 3-(3-carboxypropylphthalate) in complex with spASADH (PDB ID 4r4j) as a guide, the various para-substituted benzylamine derivatives were modeled into the active site. This enzyme structure contains an adjacent pocket near the active site, surrounded by several hydrophobic amino acids (Leu326, Ala330, Ala331 and Val14) that could make favorable interactions with the para-hydrophobic substituents of the most potent inhibitors. Without wishing to be bound by theory, it is believed the shape of this hydrophobic pocket could also accommodate a para-substituent as large as biphenyl, but interactions with hydrophobic substituents at either the ortho- or meta-position are less favorable. The Val14 in this putative binding pocket is fully conserved throughout the ASADH family. However, in the corresponding region in the structure of vcASADH (PDB ID 2qz9), several substitutions with charged or polar amino acids, including Arg and Asn in the 326 to 331 loop, would make this pocket much less hydrophobic and explain the failure of these particular inhibitors to show improved affinity with this Gram-negative ortholog of ASADH.

Materials and Methods

All compounds and reagents purchased from commercial sources were used without further purification. Reaction progress was monitored by TLC carried out using silica coated glass plates (Analtech) and was visualized by 254 nm UV light. Hash column chromatography was conducted in a 20 mm×250 mm column with 40-63µ SiliaFlash P60 silica gel (Silicycle) using the specified ethyl acetate:hexanes gradient for elution. $^1$H NMR spectra were recorded on either a Varian VXRS 400 MHz or a Varian INOVA 600 MHz spectrometer, and were calibrated using residual non-deuterated solvent as an internal reference (CDCl$_3$, δ=7.26, for the esters; D$_2$O, δ=4.80, for the sodium salts).

Synthesis of 4-methylphthalate dimethyl ester (1Me)

To a solution of compound 1, 4-methyl-1,2-dicarboxylic acid (5 g, 27.7 mmol) in 12 ml of methanol, 5 ml of sulfuric acid was added at r. t. The reaction mixture was allowed to stir in a microwave reactor at 80° C. for 8 h. Saturated NaHCO$_3$ solution was added to the reaction mixture until slightly basic, with the product precipitating as an oily liquid. The product was extracted with several portions of dichloromethane (DCM), dried over anhydrous sodium sulphate, and concentrated in vacuum. The compound was purified by column chromatography using 0-10% ethyl acetate:hexanes to yield ester 1Me. $^1$H NMR (600 MHz, CDCl$_3$): δ=2.39 (s, 3H), 3.87 (s, 3H), 3.88 (s, 3H), 7.30 (d, J=7.8 Hz, 1H), 7.45 (s, 1H), 7.65 (d, J=7.8 Hz, 1H). MS (ESI) m/z: (obs) [M+Na]$^+$231.1, (calc) 231.2.

Synthesis of 4-bromomethylphthalate dimethyl ester (2Me)

To a solution of compound 2 (5 g, 24.8 mmol) in 25 ml dichloromethane was added NBS (4.9 g, 27.3 mmol). The reaction mixture was stirred in the presence of light for 3 h, concentrated under vacuum and purified by flash column chromatography using 0-20% ethyl acetate:hexanes to obtain compound 2Me. $^1$H NMR (600 MHz, CDCl$_3$): δ=3.89 (s, 6H), 4.46 (s, 2H), 7.53 (d, J=6.6 Hz, 1H), 7.68-7.71 (m, 2H). MS (ESI) m/z: (obs) [M+Na]$^+$ (isotopic) 309.3, 311.1 (calc) (isotopic) 309.0, 311.0.

Synthesis of N-carboxymethyl-3,4-dicarboxybenzylamine (3)

To a solution of compound 2Me (3.1 g, 10.7 mmol) in DMF was added NaHCO$_3$ (4.6 g, 54 mmol) and glycine methyl ester hydrochloride (6.8 g, 54 mmol). The reaction mixture was stirred at r. t. for 8 h. DMF was air evaporated and the reaction mixture was purified by flash column chromatography using 10-50% ethyl acetate:hexanes to obtain compound 3Me. $^1$H NMR (600 MHz, CDCl$_3$): δ=3.38 (s, 2H), 3.70 (s, 3H) 3.84 (s, 2H), 3.86-3.87 (s, 6H), 7.48 (d, J=7.8 Hz, 1H), 7.64 (s, 1H), 7.68 (d, J=7.8 Hz, 2H). MS (ESI) m/z: (obs) [M+Na]$^+$ 318.4, (calc) 318.3. This ester was hydrolyzed by adding H$_2$O (0.1 ml) to a solution of compound 3Me (0.04 g, 0.14 mmol) in THF (0.4 ml). Then 1 N NaOH (0.4 ml, 0.42 mmol) was added to the reaction mixture and stirred at r. t. for 3 h. The reaction mixture was concentrated and dried for several hours under high vacuum to yield pure compound 3. $^1$H NMR (400 MHz, D$_2$O): δ=3.12 (s, 2H), 3.66 (s, 2H), 7.48 (d, J=7.8 Hz, 1H), 7.27-7.32 (m, 2H), 7.40 (s, 1H).

Synthesis of N-carboxyethyl-3,4-dicarboxybenzylamine (4)

To a solution of compound 2Me (0.52 g, 1.8 mmol) in DMF was added NaHCO$_3$ (0.8 g, 9 mmol) and β-alanine methyl ester hydrochloride (1.3 g, 9 mmol). The reaction mixture was stirred at r. t. for 8 h. DMF was air evaporated and the reaction mixture was purified by flash column chromatography using 10-60% ethyl acetate:hexanes to obtain compound 4Me. $^1$H NMR (600 MHz, CDCl$_3$):

δ=3.38 (s, 2H), 3.70 (s, 3H), 3.84 (s, 2H), 3.86 (s, 3H), 3.87 (s, 3H), 7.48 (d, J=7.8 Hz, 1H), 7.64 (s, 1H), 7.68 (d, J=7.8 Hz, 2H). MS (ESI) m/z: (obs) [M+Na]$^+$ 332.4, (calc) 332.3. A solution of compound 4Me (0.071 g, 0.229 mmol) was base-hydrolyzed as described above to yield pure compound 4. $^1$H NMR (600 MHz, D$_2$O): δ=2.47 (t, J=7.2 Hz, 2H), 2.66 (t, J=7.2 Hz, 2H), 3.59 (s, 2H), 7.18 (d, J=7.8 Hz, 1H), 7.21 (s, 1H), 7.30 9 (d, J=7.8 Hz, 1H).

Synthesis of N-((2-methyl)carboxymethyl)-3,4-dicarboxybenzylamine (5)

To a solution of compound 2Me (1.36 g, 4.7 mmol) in DMF was added NaHCO$_3$ (2.0 g, 23.7 mmol) and L-alanine methyl ester hydrochloride (3.3 g, 23.7 mmol). The reaction mixture was stirred at r. t. for 8 h. DMF was air evaporated and the reaction mixture was purified by flash column chromatography using 10-60% ethyl acetate:hexanes to obtain compound 5Me. $^1$H NMR (600 MHz, CDCl$_3$): δ=1.32 (d, J=6.6 Hz 3H), 3.49 (m, J=6.6 Hz 1H), 3.71 (s, 4H), 3.84 (s, 2H), 3.87-3.90 (m, 8H), 7.51 (d, J=7.8 Hz 1H), 7.66 (s, 1H), 7.69 (d, J=7.8 Hz, 1H). MS (ESI) m/z: (obs) [M+Na]$^+$ 332.4, (calc) 332.3. A solution of compound 5Me (0.071 g, 0.229 mmol) was base-hydrolyzed as described above to yield pure compound 5. $^1$H NMR (600 MHz, D$_2$O): δ=1.16 (d, J=6.6 Hz 3H), 3.11 (m, J=7.2 Hz 1H), 3.52 (d, J=12.6 Hz 1H), 3.68 (d, J=12.6 Hz 1H), 7.27 (d, J=8.4 Hz 1H), 7.31 (s, 1H), 7.40 (d, J=7.8 Hz, 1H).

Synthesis of N-((2-hydroxymethyl)carboxymethyl)-3,4-dicarboxybenzylamine (6)

To a solution of compound 2Me (1.15 g, 4.0 mmol) in DMF was added NaHCO$_3$ (1.7 g, 20.1 mmol) and L-serine methyl ester hydrochloride (3.1 g, 20.1 mmol). The reaction mixture was stirred at r. t. for 8 h. DMF was air evaporated and the reaction mixture was purified by flash column chromatography using 10-60% ethyl acetate:hexanes to obtain compound 6Me. $^1$H NMR (600 MHz, CDCl$_3$): δ=2.43 (s, 2H), 3.39 (m, 1H), 3.64 (m, 1H), 3.74 (s, 3H), 3.80 (m, 2H), 3.81-3.89 (m, 6H), 3.95 (d, J=14.4 Hz 1H), 7.50 (d, J=7.8 Hz, 1H), 7.66 (s, 1H), 7.70 (d, J=7.8 Hz, 1H). MS (ESI) m/z: (obs) [M+Na]$^+$ 348.4, (calc) 348.3. A solution of compound 6Me (0.071 g, 0.229 mmol) was base-hydrolyzed as described above to yield pure compound 6. $^1$H NMR (600 MHz, D$_2$O): δ=3.17 (t, J=5.2 Hz 1H), 3.61 (d, 13.2 Hz 1H), 3.68-3.70 (m, 2H), 3.78 (d, J=12.8 Hz 1H), 7.31 (d, J=8 Hz, 1H), 7.35 (s, 1H), 7.42 (d, J=7.8 Hz, 1H).

Synthesis of 3-methylphthalate dimethyl ester (7Me)

To a solution of compound 7, 3-methylphthalic acid (5 g, 24 mmol) in 12 ml of methanol at r. t. was added 5 ml of conc. sulfuric acid, with the reaction mixture stirred in a microwave reactor at 80° C. for 8 h. Saturated NaHCO$_3$ solution was added to the reaction mixture until slightly basic, and the product was extracted with DCM and concentrated in vacuum. The compound was purified by column chromatography using 0-10% ethyl acetate:hexanes to furnish ester 7Me. NMR (600 MHz, CDCl$_3$): δ=2.33 (s, 3H), 3.87 (s, 3H), 3.93 (s, 3H), 7.35 (t, J=7.8 Hz, 1H), 7.39 (d, J=7.8 Hz, 1H), 7.80 (d, J=7.2 Hz, 1H). MS (ESI) m/z: (obs) [M+Na]$^+$ 231.1, (calc) 231.2.

Synthesis of 3-bromomethylphthalate dimethyl ester (8Me)

To a solution of compound 7Me (1.8 g, 8.8 mmol) in dichloromethane was added NBS (1.72 g, 9.7 mmol). The reaction mixture was stirred in presence of light for 3 h, concentrated in vacuum and purified by flash column chromatography using 0-15% ethyl acetate:hexanes to obtain compound 8Me. $^1$H NMR (600 MHz, CDCl$_3$): δ=3.88 (s, 3H), 3.95 (s, 3H), 4.52 (s, 2H), 7.46 (t, J=7.8 Hz, 1H), 7.61 (d, J=7.8 Hz, 1H), 7.90 (d, J=7.8 Hz, 1H). MS (ESI) m/z: (obs) [M+Na]$^+$ (isotopic) 309.2, 311.1 (calc) (isotopic) 309.0, 311.0.

Synthesis of N-methyl, N-carboxymethyl-2,3-dicarboxybenzylamine (9)

To a solution of compound 8Me (0.42 g, 1.46 mmol) in DMF was added NaHCO$_3$ (0.61 g, 7.32 mmol) and N-methyl glycine methyl ester hydrochloride (1.1 g, 7.35 mmol). The reaction mixture was stirred at r. t. for 8 h. DMF was air evaporated and the reaction mixture was purified by flash column chromatography on silica gel using 10-40% ethyl acetate:hexanes to obtain compound 9Me. $^1$H NMR (600 MHz, CDCl$_3$): δ=2.23 (s, 3H), 3.15 (s, 2H), 3.57 (s, 3H), 3.65 (s, 2H), 3.76 (s, 3H), 3.78 (s, 3H), 7.31 (t, J=7.8 Hz, 1H), 7.54 (d, J=7.8 Hz, 1H), 7.76 (d, J=7.8 Hz, 1H). MS (ESI) m/z: (obs) [M+Na]$^+$332.4, (calc) 332.3. This ester was hydrolyzed as described above to yield pure compound 9. $^1$H NMR (600 MHz, D$_2$O): δ=2.10 (s, 3H), 2.98 (s, 2H), 3.55 (s, 2H), 7.29 (t, J=7.2 Hz, 1H), 7.50 (d, J=7.2 Hz, 1H), 7.53 (d, J=7.2 Hz, 1H).

General Protocol for the Synthesis of N-Derivatized Dicarboxybenzylamines (10-34)

To a solution of compound 3Me (1 eq.) in acetonitrile was added 1.1 eq of various alkyl halides (FIG. 4, Table 1) or various benzyl halides (FIG. 5, Table 2) along with 1.1 eq of NaHCO$_3$. The reaction mixture was stirred at r. t. for 3 h. CH$_3$CN was evaporated in vacuum and purified by flash column chromatography on silica gel using 0-25% ethyl acetate:hexanes to obtain corresponding N-derivatized benzylamine esters. Ester hydrolysis was carried out by adding 0.1 ml of H$_2$O to a solution of N-derivatized benzylamine esters (1 eq) in THF (0.4 ml) with stirring. Then, 1 N NaOH (3.3 eq) was added to the reaction mixture and stirred at r. t. for 3 h. The reaction mixture was concentrated and dried for several hours under high vacuum to yield the corresponding sodium salts of the N-derivatized benzylamines, compounds 10-34.

N-methyl, N-carboxymethyl-3,4-dicarboxybenzylamine (10)

Triester: $^1$H NMR (600 MHz, CDCl$_3$): δ=2.36 9s, 3H), 3.28 (s, 2H), 3.69 (s, 3H) 3.73 (s, 2H), 3.88 (s, 6H), 7.52 (d, J=7.8 Hz, 1H), 7.66 (s, 1H), 7.68 (d, J=7.8 Hz, 2H). MS (ESI) m/z: (obs) [M+Na]$^+$ 332.4, (calc) 332.3. Sodium salt: $^1$H NMR (600 MHz, D$_2$O): δ=2.04 (s, 3H), 2.85 (s, 2H), 3.46 (s, 2H), 7.15-7.17 (m, J=7.2 Hz, 2H), 7.25 (d, J=7.2 Hz, 1H).

N-allyl, N-carboxymethyl-3,4-dicarboxybenzylamine (11)

Triester: $^1$H NMR (600 MHz, CDCl$_3$): δ=3.24 (s, 2H), 3.31 (s, 2H), 3.66 (s, 3H) 3.82 (s, 2H), 3.88-3.89 (s, 6H), 5.13-5.21 (m, 2H), 5.78-5.84 (m, 1H) 7.54 (d, J=7.8 Hz, 1H), 7.68 (m, J=7.8 Hz, 2H). MS (ESI) m/z: (obs) [M+Na]$^+$ 358.4, (calc) 358.3. Sodium salt: $^1$H NMR (600 MHz, D$_2$O): δ=2.9 (s, 2H), 3.04 (s, 2H), 3.58 (s, 2H), 5.02-5.07 (m, 2H), 5.69-5.73 (m, 1H), 7.15-7.17 (m, 2H), 7.25 (d, 1H).

N-acetonitrile, N-carboxymethyl-3,4-dicarboxybenzylamine (12)

Triester: $^1$H NMR (400 MHz, CDCl$_3$): δ=3.42 (s, 2H), 3.68 (s, 2H), 3.72 (s, 3H) 3.84 (s, 2H), 3.89 (s, 6H), 7.55 (d, J=7.6 Hz, 1H), 7.7 (m, J=7.6 Hz, 2H). MS (ESI) m/z: (obs) [M+Na]$^+$ 357.4, (calc) 357.3. Sodium salt: $^1$H NMR (400 MHz, D$_2$O): δ=2.97 (s, 2H), 2.99 (s, 2H), 3.57 (s, 2H), 7.17-7.20 (m, 2H), 7.27 (d, 1H).

N-benzyl, N-carboxymethyl-3,4-dicarboxybenzylamine (13)

Triester: $^1$H NMR (400 MHz, CDCl$_3$): δ=3.30 (s, 2H), 3.68 (s, 3H), 3.79 (s, 2H), 3.87 (s, 2H), 3.89 (s, 3H), 3.91 (s, 3H), 7.23-7.34 (m, 5H), 7.59 (d, J=8 Hz, 1H), 7.72 (m, J=8 Hz, 2H). MS (ESI) m/z: (obs) [M+Na]$^+$ 408.3, (calc) 408.4. Sodium salt: $^1$H NMR (600 MHz, D$_2$O): δ=2.88 (s, 2H), 3.62 (s, 4H), 7.20 (m, 7H), 7.29 (m, 1H).

N-(1-naphthyl)-N-carboxymethyl-3,4-dicarboxybenzylamine (14)

Triester: $^1$H NMR (600 MHz, CDCl$_3$): δ=3.28 (s, 2H), 3.67 (s, 3H), 3.87 (s, 2H), 3.89 (s, 3H), 3.91 (s, 3H), 4.26 (s, 2H), 7.38 (s, J=7.8 Hz, 1H), 7.44-7.53 (m, 4H), 7.65 (m, J=7.8 Hz, 2H), 7.75 (d, J=8.4 Hz, 1H), 7.81 (d, J=8 Hz, 1H). MS (ESI) m/z: (obs) [M+Na]$^+$ 458.2, (calc) 458.5. Sodium salt: 41 NMR (600 MHz, D$_2$O): δ=3.05 (s, 2H), 3.88 (s, 2H), 4.18 (s, 2H), 7.32 (d, 1H), 7.38 (s, 1H), 7.41-7.49 (m, 5H), 7.83 (d, J=7.8 Hz, 1H), 7.88-7.90 (m, J=7.8 Hz, 1H), 7.93 (d, J=8.4 Hz, 1H).

N-(2-naphthyl)-N-carboxymethyl-3,4-dicarboxybenzylamine (15)

Triester: $^1$H NMR (600 MHz, CDCl$_3$): δ=3.32 (s, 2H), 3.67 (s, 3H), 3.87 (s, 2H), 3.88-3.90 (m, 8H), 3.91 (s, 3H), 3.94 (s, 2H), 7.43-7.45 (m, 2H), 7.51 (d, J=8.4 Hz, 2H), 7.61 (d, J=7.2 Hz, 1H), 7.70-7.74 (m, 3H), 7.79 (d, J=8.4 Hz, 3H). MS (ESI) m/z: (obs) [M+Na]$^+$ 458.2, (calc) 458.5. Sodium salt: $^1$H NMR (600 MHz, D$_2$O): δ=3.06 (s, 2H), 3.78 (s, 2H), 3.89 (s, 2H), 7.30 (d, J=7.8 Hz, 1H), 7.34 (s, 1H), 7.41 (d, J=7.8 Hz, 1H), 7.47-7.51 (m, 3H), 7.80 (s, 1H), 7.86-7.89 (m, J=7.8 Hz, 1H).

N-(ethylmorpholino)-N-carboxymethyl-3,4-dicarboxybenzylamine (16)

Triester: $^1$H NMR (600 MHz, CDCl$_3$): δ=2.38 (s, 3H), 2.44 (t, J=6.6 Hz, 2H), 2.77 (t, J=6.6 Hz, 2H), 3.39 (s, 2H), 3.64 (s, 6H), 3.85-3.86 (m, 8H), 7.49 (d, J=7.8 Hz, 2H), 7.64-7.66 (m, 3H). MS (ESI) m/z: (obs) [M+H]$^+$ 408.3, (calc) 408.4. Sodium salt: $^1$H NMR (600 MHz, D$_2$O): δ=2.40 (s, 4H), 2.46 (t, J=8.4 Hz, 2H), 2.67 (t, J=7.2 Hz, 2H), 3.09 (s, 2H), 3.64 (s, 4H), 3.69 (s, 2H), 7.32 (d, J=6.6 Hz, 2H), 7.40 (d, J=8.4 Hz, 1H).

N-(4-biphenyl)-N-carboxymethyl-3,4-dicarboxybenzylamine (17)

Triester: $^1$H NMR (600 MHz, CDCl$_3$): δ=3.33 (s, 2H), 3.68 (s, 3H), 3.83 (s, 2H), 3.88-3.91 (m, 8H), 7.31-7.33 (m, J=7.2 Hz 1H), 7.40-7.43 (m, J=7.2 Hz 1H), 7.54 (d, J=7.2 Hz, 2H), 7.58 (d, J=7.2 Hz, 2H), 7.61 (d, J=7.8 Hz, 1H), 7.71-7.73 (m, 2H). MS (ESI) m/z: (obs) [M+Na]$^+$ 484.2, (calc) 484.5. Sodium salt: $^1$H NMR (600 MHz, D$_2$O): δ=3.03 (s, 2H), 3.74 (d, J=14.4 Hz 4H), 7.31-7.33 (m, J=7.2 Hz 1H), 7.29 (d, 1H), 7.33-7.37, (m, J=7.2 Hz, 2H), 7.39-7.42 (t, J=8.4 Hz, 3H), 7.44-7.46 (t, J=7.8 Hz, 2H), 7.60 (d, J=7.8 Hz, 2H), 7.73 (d, J=7.8 Hz, 2H).

N-(2-bromobenzyl)-N-carboxymethyl-3,4-dicarboxybenzylamine (18)

Triester: $^1$H NMR (600 MHz, CDCl$_3$): δ=3.31 (s, 2H), 3.67 (s, 3H), 3.86-3.88 (s, 6H), 3.92 (s, 4H), 7.08 (t, Hz, 1H), 7.25 (t, J=7.6 Hz, 1H), 7.49 (t, J=8.0 Hz, 2H), 7.54 (d, J=8.0 Hz, 1H), 7.68 (d, J=7.6 Hz, 2H). MS (ESI) m/z: (obs) [M+Na]$^+$ (isotopic) 486.2, 488.0 (calc) (isotopic) 486.1, 488.1. Sodium salt: $^1$H NMR (600 MHz, D$_2$O): δ=3.07 (s, 2H), 3.89 (s, 2H), 3.90 (s, 2H), 7.13-7.17 (t, 1H), 7.31-7.36 (m, J=7.2 Hz, 3H), 7.39 (d, J=8 Hz, 2H), 7.56 (d, J=8 Hz, 2H).

N-(3-bromobenzyl)-N-carboxymethyl-3,4-dicarboxybenzylamine (19)

Triester: $^1$H NMR (600 MHz, CDCl$_3$): δ=3.26 (s, 2H), 3.65 (s, 3H), 3.73 (s, 2H), 3.83 (s, 2H), 3.86-3.88 (s, 6H), 7.14 (d, J=7.8 Hz, 1H), 7.24 (d, J=7.8 Hz, 1H), 7.33 (d, J=7.8 Hz, 1H), 7.48 (s, 1H), 7.54 (d, J=7.8 Hz, 1H), 7.68 (d, J=7.8 Hz, 2H). MS (ESI) m/z: (obs) [M+Na]$^+$ (isotopic) 486.2, 488.0 (calc) (isotopic) 486.1, 488.1. Sodium salt: $^1$H NMR (600 MHz, D$_2$O): δ=3.01 (s, 2H), 3.70 (s, 2H), 3.74 (s, 2H), 7.22 (t, J=7.2 Hz, 1H), 7.27-7.31 (m, 3H), 7.41 (d, J=7.8 Hz, 1H), 7.43-7.45 (d, J=7.8 Hz, 1H), 7.51 (d, 1H).

N-(4-bromobenzyl)-N-carboxymethyl-3,4-dicarboxybenzylamine (20)

Triester: $^1$H NMR (600 MHz, CDCl$_3$): δ=3.25 (s, 2H), 3.65 (s, 3H), 3.71 (s, 2H), 3.82 (s, 2H), 3.87-3.89 (s, 6H), 7.20 (d, J=7.8 Hz, 2H), 7.42 (d, J=7.8 Hz, 2H), 7.54 (d, J=7.8 Hz, 1H), 7.66-7.69 (m, J=7.8 Hz, 2H). MS (ESI) m/z: (obs) [M+Na]$^+$ (isotopic) 486.2, 488.0 (calc) (isotopic) 486.1, 488.1. Sodium salt: $^1$H NMR (600 MHz, D$_2$O): δ=2.78 (s, 2H), 3.45 (s, 2H), 3.46 (s, 2H), 6.97 (d, J=8.4 Hz, 2H), 7.05-7.07 (d, J=7.8 Hz, 1H), 7.12 (s, 1H), 7.21-7.24 (m, J=7.8 Hz, 3H).

N-(2-methylbenzyl)-N-carboxymethyl-3,4-dicarboxybenzylamine (21)

Triester: $^1$H NMR (600 MHz, CDCl$_3$): δ=2.31 (s, 3H), 3.24 (s, 2H), 3.65 (s, 3H), 3.80 (s, 2H), 3.87 (s, 2H), 3.88-3.89 (s, 6H), 7.13 (m, 3H), 7.28 (d, J=6.6 Hz, 1H), 7.52 (d, J=7.8 Hz, 1H) 7.64 (s, 1H), 7.68 (d, J=7.8 Hz, 1H). MS (ESI) m/z: (obs) [M+Na]$^+$ 422.2, (calc) 422.4. Sodium salt: $^1$H NMR (600 MHz, D$_2$O): δ=2.13 (s, 3H), 3.04 (s, 2H), 3.73 (s, 2H), 3.82 (s, 2H), 7.17 (m, 3H), 7.31-7.33 (m, 3H), 7.41 (d, J=7.8 Hz, 1H).

N-(3-methylbenzyl)-N-carboxymethyl-3,4-dicarboxybenzylamine (22)

Triester: $^1$H NMR (600 MHz, CDCl$_3$): δ=2.31 (s, 3H), 3.28 (s, 2H), 3.66 (s, 3H), 3.73 (s, 2H), 3.84 (s, 2H), 3.87-3.88 (s, 6H), 7.03 (d, J=7.8 Hz, 1H), 7.12 (d, J=7.8 Hz, 3H), 7.18 (m, J=7.8 Hz, 1H), 7.57 (d, J=7.8 Hz, 1H), 7.68 (d, J=7.8 Hz, 2H). MS (ESI) m/z: (obs) [M+Na]$^+$ 422.2, (calc) 422.4. Sodium salt: $^1$H NMR (600 MHz, D$_2$O): δ=2.28 (s, 3H), 3.01 (s, 2H), 3.70 (s, 2H), 3.74 (s, 2H), 7.12-7.16 (m, J=6 Hz, 2H), 7.16 (s, 1H), 7.24-7.26 (t, J=7.2 Hz, 1H), 7.29-7.31 (m, 2H), 7.41-7.42 (d, J=7.8 Hz, 1H).

N-(4-methylbenzyl)-N-carboxymethyl-3,4-dicarboxybenzylamine (23)

Triester: $^1$H NMR (600 MHz, CDCl$_3$): δ=2.31 (s, 3H), 3.27 (s, 2H), 3.66 (s, 3H), 3.73 (s, 2H), 3.87-3.89 (s, 6H), 7.11 (d, J=7.8 Hz, 2H), 7.22 (d, J=7.8 Hz, 2H), 7.58 (d, J=7.8 Hz, 1H), 7.69-7.70 (m, J=7.8 Hz, 2H). MS (ESI) m/z: (obs) [M+Na]$^+$ 422.2, (calc) 422.4. Sodium salt: $^1$H NMR (600 MHz, D$_2$O): δ=2.27 (s, 3H), 2.96 (s, 2H), 3.70 (s, 2H), 3.72 (s, 2H), 7.18-7.22 (m, J=7.8 Hz, 4H), 7.28-7.30 (m, 2H), 7.40 (d, J=7.8 Hz, 1H).

N-(2-trifluoromethylbenzyl)-N-carboxymethyl-3,4-dicarboxybenzylamine (24)

Triester: $^1$H NMR (600 MHz, CDCl$_3$): δ=3.28 (s, 2H), 3.66 (s, 3H), 3.86 (s, 2H), 3.86-3.88 (s, 6H), 3.95 (s, 2H), 7.31 (t, J=7.8 Hz, 1H), 7.51 (t, J=7.8 Hz, 1H), 7.57 (t, J=7.8 Hz, 2H) 7.68 (m, J=7.8 Hz, 2H), 7.85 (d, J=7.8 Hz, 1H). MS (ESI) m/z: (obs) [M+Na]$^+$ 476.1, (calc) 476.4. Sodium salt: 41 NMR (600 MHz, D$_2$O): δ=3.05 (s, 2H), 3.79 (s, 2H), 3.91 (s, 2H), 7.33 (m, 2H), 7.36-7.40 (m, 2H), 7.56 (t, J=7.8 Hz, 1H), 7.65 (d, J=7.8 Hz, 1H), 7.78 (d, J=7.8 Hz, 1H).

N-(3-trifluoromethylbenzyl)-N-carboxymethyl-3,4-dicarboxybenzylamine (25)

Triester: $^1$H NMR (600 MHz, CDCl$_3$): δ=3.29 (s, 2H), 3.66 (s, 3H), 3.83 (s, 2H), 3.85 (s, 2H), 3.86-3.89 (s, 6H), 7.40 (t, J=7.8 Hz, 1H), 7.49 (d, J=7.8 Hz, 1H), 7.53 (t, J=7.8 Hz, 2H) 7.57 (s, J=7.8 Hz, 1H), 7.68 (d, J=7.8 Hz, 2H). MS (ESI) m/z: (obs) [M+Na]$^+$ 476.1, (calc) 476.4. Sodium salt: $^1$H NMR (600 MHz, D$_2$O): δ=3.03 (s, 2H), 3.75 (s, 2H), 3.80 (s, 2H), 7.29-7.32 (m, J=6 Hz, 2H), 7.16 (s, 1H), 7.41 (d, J=7.8 Hz, 1H), 7.48-7.51 (t, J=7.8 Hz, 1H), 7.55 (d, J=7.8 Hz, 1H), 7.59 (s, 1H), 7.65 (s, 1H).

N-(4-trifluoromethylbenzyl)-N-carboxymethyl-3,4-dicarboxybenzylamine (26)

Triester: $^1$H NMR (600 MHz, CDCl$_3$): δ=3.28 (s, 2H), 3.66 (s, 3H), 3.83 (s, 2H), 3.87 (s, 3H), 3.89 (s, 3H), 7.45 (d, J=7.8 Hz, 2H), 7.54-7.56 (m, J=7.8 Hz, 3H), 7.68-7.70 (m, J=7.8 Hz, 2H). MS (ESI) m/z: (obs) [M+Na]$^+$ 476.1, (calc) 476.4. Sodium salt: $^1$H NMR (600 MHz, D$_2$O): δ=2.89 (s, 2H), 3.61 (s, 2H), 3.66 (s, 2H), 7.16 (m, J=8.4 Hz, 2H), 7.27 (d, J=7.2 Hz, 1H), 7.33 (d, J=6 Hz, 2H), 7.50 (d, J=6.6 Hz, 2H).

N-(2-trifluoromethyoxybenzyl)-N-carboxymethyl-3,4-dicarboxybenzylamine (27)

Triester: $^1$H NMR (600 MHz, CDCl$_3$): δ=3.27 (s, 2H), 3.65 (s, 3H), 3.86 (s, 2H), 3.87 (s, 2H), 3.88 (s, 6H), 7.19 (d, J=7.8 Hz, 1H), 7.25 (m, J=7.8 Hz, 2H), 7.55 (m, J=7.8 Hz, 2H) 7.68 (d, J=7.8 Hz, 2H). MS (ESI) m/z: (obs) [M+Na]$^+$ 492.1, (calc) 492.4. Sodium salt: $^1$H NMR (600 MHz, D$_2$O): δ=3.03 (s, 2H), 3.82 (s, 2H), 3.87 (s, 2H), 7.30-7.36 (m, 5H), 7.40 (d, J=7.2 Hz, 1H), 7.45 (d, J=7.8 Hz, 1H).

N-(3-trifluoromethoxybenzyl)-N-carboxymethyl-3,4-dicarboxybenzylamine (28)

Triester: $^1$H NMR (600 MHz, CDCl$_3$): δ=3.28 (s, 2H), 3.65 (s, 2H), 3.79 (s, 2H), 3.84 (s, 2H), 3.86-3.88 (s, 6H), 7.06 (d, J=7.8 Hz, 1H), 7.24 (s, J=7.8 Hz, 1H), 7.30 (t, J=7.8 Hz, 2H), 7.57 (D, J=7.8 Hz, 1H), 7.68 (d, J=7.8 Hz, 2H). MS (ESI) m/z: (obs) [M+Na]$^+$ 492.1, (calc) 492.4. Sodium salt: $^1$H NMR (600 MHz, D$_2$O): δ=3.03 (s, 2H), 3.75 (s, 2H), 3.77 (s, 2H), 7.21 (d, J=7.8 Hz, 1H), 7.28-7.32 (m, 4H), 7.39-7.42 (m, J=7.8 Hz, 2H).

N-(4-trifluoromethoxybenzyl)-N-carboxymethyl-3,4-dicarboxybenzylamine (29)

Triester: $^1$H NMR (600 MHz, CDCl$_3$): δ=3.27 (s, 2H), 3.66 (s, 3H), 3.76 (s, 2H), 3.84 (s, 2H), 3.87 (s, 3H), 3.89 (s, 3H), 7.13 (d, J=8.4 Hz, 2H), 7.35 (d, J=8.4 Hz, 2H), 7.54 (d, J=8.4 Hz, 1H), 7.67-7.69 (m, J=8.4 Hz, 2H). MS (ESI) m/z: (obs) [M+Na]$^+$ 492.1, (calc) 492.4. Sodium salt: $^1$H NMR (600 MHz, D$_2$O): δ=2.87 (s, 2H), 3.60 (s, 4H), 6.48-6.73 (m, 1H), 7.11 (d, J=6 Hz, 2H), 7.16 (m, J=6 Hz, 2H), 7.22 (m, J=6 Hz, 2H), 7.26 (m, J=6 Hz, 1H).

N-(4-difluoromethoxybenzyl)-N-carboxymethyl-3,4-dicarboxybenzylamine (30)

Triester: $^1$H NMR (600 MHz, CDCl$_3$): δ=3.26 (s, 2H), 3.65 (s, 3H), 3.74 (s, 2H), 3.83 (s, 2H), 3.86-3.88 (s, 6H), 6.34-6.59 (m, 1H), 7.02 (d, J=8.4 Hz, 2H), 7.31 (d, J=8.4 Hz, 2H), 7.54 (d, J=8.4 Hz, 1H), 7.66-7.69 (m, J=8.4 Hz, 2H). MS (ESI) m/z: (obs) [M+Na]$^+$ 474.2, (calc) 474.4. Sodium salt: $^1$H NMR (600 MHz, D$_2$O): δ=2.86 (s, 2H), 3.57 (s, 2H), 3.60 (s, 2H), 6.48-6.73 (m, 1H), 6.95 (d, J=8.4 Hz, 2H), 7.13-7.18 (m, J=8.4 Hz, 4H), 7.24 (m, J=7.8 Hz, 1H).

N-(4-carboxybenzyl)-N-carboxymethyl-3,4-dicarboxybenzylamine (31)

Triester: $^1$H NMR (600 MHz, CDCl$_3$): δ=3.26 (s, 2H), 3.64 (s, 3H), 3.81 (s, 2H), 3.83 (s, 2H), 3.85 (s, 3H), 3.86 (s, 3H), 3.87 (s, 3H), 7.39 (d, J=8.4 Hz, 2H), 7.54 (d, J=8.4 Hz, 1H), 7.66-7.68 (m, J=8.4 Hz, 2H), 7.94 (d, J=8.4 Hz, 2H). MS (ESI) m/z: (obs) [M+Na]$^+$ 466.2, (calc) 466.4. Sodium salt: $^1$H NMR (600 MHz, D$_2$O): δ=2.83 (s, 2H), 3.54 (s, 2H), 3.58 (s, 2H), 7.11 (d, 2H), 7.17-7.19 (m, 3H), 7.25 (d, 1H), 7.61 (d, 2H).

N-(4-carboxamidebenzyl)-N-carboxymethyl-3,4-dicarboxybenzylamine (32)

Triester: $^1$H NMR (600 MHz, CDCl$_3$): δ=3.27 (s, 2H), 3.65 (s, 3H), δ=4.07 (m, 2H), 3.79-3.82 (m, 4H), 3.85-3.87 (s, 6H), 6.19-6.36 (m, 2H), 7.37 (d, J=7.8 Hz, 2H), 7.53 (d, J=7.2 Hz, 1H), 7.64-7.66 (m, 2H), 7.72 (d, J=8.4 Hz, 2H). MS (ESI) m/z: (obs) [M+Na]$^+$ 451.3, (calc) 451.4. Sodium salt: $^1$H NMR (600 MHz, D$_2$O): δ=3.02 (s, 2H), 3.77-3.79 (m, 4H), 7.31-7.34 (M, 2H), 7.37 (d, J=7.8 Hz, 2H), 7.41 (d, J=7.8 Hz, 1H), 7.78 (d, J=8.4 Hz, 2H).

N-(4-t-butylbenzyl)-N-carboxymethyl-3,4-dicarboxybenzylamine (33)

Triester: $^1$H NMR (400 MHz, CDCl$_3$): δ=1.30 (s, 9H), 3.31 (s, 2H), 3.67 (s, 3H), 3.77 (s, 2H), 3.87 (s, 2H), 3.88-3.91 (s, 6H), 7.27 (d, J=8 Hz, 2H), 7.34 (d, J=8 Hz, 2H), 7.59 (d, J=8 Hz, 1H), 7.61 (d, J=7.6 Hz, 2H). MS (ESI) m/z: (obs) [M+Na]$^+$ 464.3, (calc) 464.5. Sodium salt: $^1$H NMR (600 MHz, D$_2$O): δ=1.26 (s, 9H), 3.01 (s, 2H), 3.73 (s, 4H), 3.66 (s, 2H), 7.16 (m, J=8.4 Hz, 2H), 7.28-7.31 (m, 3H), 7.34 (s, 1H), 7.41-7.43 (d, J=7.8 Hz, 1H), 7.44-7.46 (d, J=7.8 Hz, 2H).

N-(4-(2-perfluoropropyl))-N-carboxymethyl-3,4-dicarboxybenzylamine (34)

Triester: $^1$H NMR (600 MHz, CDCl$_3$): δ=3.30 (s, 2H), 3.66 (s, 3H), 3.84 (s, 2H), 3.87-3.88 (m, 8H), 7.47 (m, J=7.8 Hz, 2H), 7.52 (m, J=8.4 Hz, 2H), 7.56 (d, J=7.8 Hz, 1H), 7.69 (m, 2H). MS (ESI) m/z: (obs) [M+Na]$^+$ 575.9, (calc) 576.4. Sodium salt: $^1$H NMR (600 MHz, D$_2$O): δ=3.07 (s, 2H), 3.77 (s, 2H), 3.83 (s, 2H), 7.33-7.34 (m, 1H), 7.39 (s, 1H), 7.45 (d, J=7.8 Hz, 1H), 7.54 (d, J=7.8 Hz, 1H), 7.68 (d, J=7.8 Hz, 2H).

Synthesis of N-(4-bromobenzyl)-N-carboxyethyl-3,4-dicarboxybenzylamine (35)

4-bromo-benzyl bromide was added to a solution of compound 4Me, followed by hydrolysis of the ester product as described above to yield compound 35. Triester: NMR (600 MHz, CDCl$_3$): δ=2.46 (t, 2H), 2.74 (t, 2H), 3.47 (s, 3H), 3.56 (s, 2H), 3.59 (s, 3H), 3.86 (s, 3H), 3.88 (s, 3H), 7.13 (d, J=7.8 Hz, 2H), 7.40 (d, J=7.8 Hz, 2H), 7.46 (d, J=7.8 Hz, 1H), 7.59 (s, 1H), 7.66 (d, J=7.8 Hz, 1H). MS (ESI) m/z: (obs) [M+Na]$^+$ (isotopic) 500.1, 501.9 (calc) (isotopic) 500.1, 502.1. Sodium salt: $^1$H NMR (600 MHz, CDCl$_3$): δ=2.43 (t, 2H), 2.73 (t, 2H), 3.54 (s, 2H), 3.59 (s, 2H), 7.19 (d, J=7.8 Hz, 2H), 7.27-7.31 (m, 2H), 7.41 (d, J=7.2 Hz, 1H), 7.48 (d, J=7.8 Hz 2H).

Synthesis of N-(4-trifluoromethylbenzyl)-N-carboxymethyl-3,4-dicarboxybenzylamine (36)

4-trifluromethylbenzyl bromide was added to a solution of compound 4Me, followed by hydrolysis of ester product as described above to yield compound 36. Triester: $^1$H NMR (600 MHz, CDCl$_3$): δ=2.48 (t, 2H), 2.77 (t, 2H), 3.58 (s, 2H), 3.59 (s, 2H), 3.60 (s, 3H), 3.86 (s, 3H), 3.88 (s, 3H), 7.40 (d, J=7.8 Hz, 2H), 7.49 (d, J=7.8 Hz, 2H), 7.52 (d, J=7.8 Hz, 1H), 7.61 (s, 1H), 7.66 (d, J=7.8 Hz, 1H). MS (ESI) m/z: (obs) [M+Na]$^+$ 490.2, (calc) 490.4. Sodium salt: $^1$H NMR (600 MHz, CDCl$_3$): δ=2.44 (t, 2H), 2.75 (t, 2H), 3.61 (s, 2H), 3.64 (s, 2H), 7.33 (d, J=7.8 Hz, 2H), 7.41-7.45 (m, 3H), 7.64 (d, J=7.8 Hz 2H).

Synthesis of N-acetal-N-carboxymethyl-3,4-dicarboxybenzylamine (37)

To a 0.8 ml solution of compound 3Me (0.15 g, 0.5 mmol) in formic acid 0.8 ml of acetic anhydride was added dropwise and the reaction mixture was refluxed at 100° C. for 1 h. The reaction mixture was cooled to r. t. and then concentrated by vacuum and diluted with DCM. The DCM portion was washed 4 times with 1 M NaHCO$_3$ and twice with water and dried over anhydrous Na$_2$SO$_4$. The concentrated product was dissolved in 0.4 ml of THF and the esters were hydrolyzed as described above to yield compound 37. Triester: $^1$H NMR (600 MHz, CDCl$_3$): δ=3.64 (s, 3H), 3.83 (s, 3H), 3.84 (s, 3H), 3.88 (S, 2H), 4.53-4.59 (m, 2H), 7.34 (d, J=6.6 Hz, 1H), 7.49 (d, J=8.4 Hz, 1H), 7.63-7.69 (m, 1H), 8.12-8.29 (m, 1H). MS (ESI) m/z: (obs) [M+Na]$^+$ 364.4, (calc) 364.3. Sodium salt: $^1$H NMR (400 MHz, D$_2$O): δ=3.0 (s, 2H), 3.55 (s, 2H), 7.15-7.19 (m, 2H), 7.27-7.29 (d, J=8 Hz, 1H), 8.26 (s, 1H).

Synthesis of N-((4-(2-benzyl)vinyl)benzyl)-N-carboxymethyl-3,4-dicarboxybenzylamine (38)

Compound 20 (0.48 g, 1.03 mmol) was weighed in a vial and bis(tri-tert-butylphosphinepalladium(0) (0.1 g, 0.19 mmol) was added under inert conditions in a nitrogen bag to the sealed vial. Then, at r. t. and under inert conditions, were sequentially added 3 ml of anhydrous toluene, N-cyclohexyl-N-methyl cyclohexylamine (0.27 ml, 1.24 mmol), and styrene (0.17 ml, 1.44 mmol). The reaction mixture was allowed for stirring in a microwave reactor at 110° C. for 16-18 h. Water was added to the reaction mixture, followed by extraction with several portions of diethyl ether, dried over anhydrous sodium sulfate and concentrated in vacuum. The product was purified by column chromatography using 0-15% ethyl acetate:hexanes. The resulting ester product was hydrolyzed as described above to yield compound 38. Triester: $^1$H NMR (600 MHz, CDCl$_3$): δ=3.3 (s, 2H), 3.67 (s, 3H), 3.78 (s, 2H), 3.86 (s, 2H), 3.88-3.90 (s, 6H), 7.08 (m, 2H), 7.25 (m, 1H), 7.32-7.35 (m, 4H), 7.45 (d, J=7.8 Hz, 2H), 7.50 (d, J=7.8 Hz, 2H), 7.60 (d, J=7.8 Hz 2H), 7.71 (d, J=8.4 Hz 2H). MS (ESI) m/z: (obs) [M+Na]$^+$ 510.2, (calc) 510.5. Sodium salt: $^1$H NMR (400 MHz, D$_2$O): δ=3.03 (s, 2H), 3.75 (s, 2H), 3.76 (s, 2H), 7.22 (m, 2H), 7.28-7.34 (m, J=7.2 Hz, 5H), 7.38-7.43 (m, J=7.8 Hz, 3H), 7.55-7.59 (d, J=7.8 Hz, 4H).

Enzyme Purification and Kinetic Assay

ASADHs from *S. pneumoniae* and *V. cholerae* were cloned, expressed, and purified. The concentrated enzymes were stored at −20° C. in a storage buffer containing 50 mM HEPES (pH 7), 1 mM EDTA, and 1 mM DTT. Because of the instability of aspartyl phosphate, the reaction was followed in the reverse direction, with the increase in the absorbance of NADPH monitored at 340 nm. Initial velocity kinetics of ASADH was carried out at r.t. in a reaction buffer composed of 120 mM CHES, pH 8.6, and 200 mM KCl, with ASA at either 0.15 mM (spASADH) or 0.3 mM (vcASADH), 1.5 mM NADP, and 20 mM phosphate in a final volume of 200 μl. Enzyme (30 μg ml$^{-1}$) was added to each well to initiate the reaction. To determine the inhibition constant (K$_i$) of each compound, inhibitor was added to each well by serial dilution to cover a suitable concentration range. The measured initial velocities were then fitted to a Dixon plot that assumes competitive inhibition against ASA to determine the K$_i$ value for each inhibitor.

Example II—ANAT Inhibitors

A set of focused compound libraries was screened in a search for inhibitors of aspartate N-acetyltransferase (ANAT). The initial libraries were composed of amino acids, amino acid derivatives, various metabolites, and metabolite analogs. Examination of 256 compounds yielded a total of 17 moderate inhibitors that showed at least 50% inhibition of ANAT when examined at a concentration of 2 mM (Table 3, FIG. 7). The most potent inhibitor from these libraries, an N-chloroacetyl derivative of the substrate, yielded a K$_i$ value of 200 μM. Next, a group of constrained amino acid analogs were examined, producing an additional set of moderate inhibitors. One compound, the N-carbobenzyloxy derivative of L-aspartate, gave an unexpectedly potent K$_i$ value of 17 μM (Table 3, FIG. 7).

Production of Phthalate Derivatives

A series of dioic acid structures, built on a conformationally-constrained phthalic acid core, is described above in Example I as having been produced and optimized as selective inhibitors of a Gram-positive form of aspartate β-semialdehyde dehydrogenase obtained from *Streptococcus pneumonia*. Given the similarity between the substrate structures of this enzyme to that of ANAT, this class of compounds was examined as inhibitors of the ANAT enzyme.

Preliminary Evaluation of Enzymatic Activity

Compounds 3 (with the shorter N-carboxymethyl side chain), 5, and 6 did not show any inhibition with ANAT. Compounds 4 (with the longer N-carboxyethyl side chain) and 9 do inhibit ANAT with a relatively weak $K_i$ of 1.7 mM (Table 4, FIG. 8) and 1.2 mM, respectively.

Introduction of Substituted Benzyl Groups

To further explore the affinity of the parent compound 3 to the ANAT enzyme, several additional derivatives were synthesized through coupling with various halides at the secondary amine position. However, the introduction of simple alkyl or nitrile (10 & 12) did not confer any inhibitory properties into these compounds (Table 4, FIG. 8). Introduction of aldehyde and allyl (11 & 37), though leading to improved inhibition, resulted in relatively weak inhibitors with $K_i$ of 1.2 and 0.71 mM, respectively. However, introduction of a benzyl (13) group did improve the inhibition, with a $K_i$ of 0.42 mM. To further explore the binding affinity, a series of substituted benzyl substituents were introduced at this amine position.

Incorporation of Hydrophobic Benzyl Substituents

Coupling with benzyl halides substituted with methyl groups at the ortho- or meta- or para-position (21-23) did not yield any improvement in affinity (Table 5, FIG. 9). Similar p-substitution with bromo or trifluoromethyl group at the para-position of the benzyl ring (20 and 26) resulted in a weaker inhibitor. But substitution with a bromo or trifluoromethyl group at the ortho- or meta-position resulted in inhibitors (18, 19, 24, and 25) with some improvement in the $K_i$ values against ANAT (Table 5, FIG. 9). Next, the effect of changes in the methyl substituent was examined Replacement of the methyl group with either —$OCF_3$ or —$OCHF_2$ groups (27-30) did not increase the affinity of these derivatives.

Examination of Additional Hydrophobic Derivatives

Changing the para substituent with bulkier substituents like p-tert-butylbenzyl (33), p-perfluoropropyl (34), 4-biphenyl (17), or N-ethylmorpholino (16) only resulted in weak inhibitors with no enhancement in the $K_i$ values (Table 4, FIG. 8). Changing the substituent to a 2-napthyl (15) group also did not improve the inhibition but, interestingly, the 1-naphthyl (14) derivative showed an improved inhibition with $K_i$ value of 115 µM (Table 4, FIG. 8).

Incorporation of Hydrophilic Benzyl Substituent

To examine the effect of a hydrophilic substituent, p-carboxyl derivative (31) was synthesized and tested against ANAT. Unlike any other para-substituted derivative, this compound showed an enhanced inhibition with $K_i$ value of 104 µM (Table 5, FIG. 9). This compound being the only better inhibitor in the para-substituted series indicates that the improved affinity for this charged benzyl derivative is due to the electrostatic interaction with a positively-charged amino acid side chain near the active site and the p-carboxyl group of the molecule. To further validate this, the p-carboxyl group was replaced with a polar but uncharged substituent. A carboxamide group (35) and a ketone (36) functionalized derivatives were tested. These derivatives lose the inhibitory properties, with poor $K_i$ values (Table 3, FIG. 6).

Introduction of Longer Chain Parent

The shorter chain parent compound 3 had no inhibitory properties, while the longer chain parent compound 4 had modest inhibitory properties against ANAT. However, several modifications and refinements on parent compound 3 yielded some sub-micromolar level inhibitors. Now that the significance of the derivatives with bromo or trifluoromethyl group at the ortho- and meta-position as decent inhibitors has been demonstrated, several longer homologs of these derivatives were synthesized starting from parent compound 4 (Scheme 1A, FIG. 2A). The o- and m-derivatives of either bromo or trifluoromethyl (53, 54 and 40, 41) (Table 5, FIG. 9) not only lead to better inhibitors but these had better $K_i$ values compared to the similar analogs of the shorter chain parent molecule. However, the methyl substituted derivatives (43 and 44) of this series did not show improved inhibition. This was the same case as observed with the methyl substituted benzyl derivatives of the shorter chain parent molecule.

Effect of Para Substituted Hydrophobic Functional Group

To scrutinize the consequence of hydrophobic functional groups at the para position of this long chain parent compound, a few selected benzyl derivatives were synthesized. p-methyl (45), p-tert-butyl (46), and p-perfluoropropyl (47) were tested, and all of them corroborate to be very poor inhibitors of ANAT. However, the corresponding p-bromo (35) and p-trifluoromethyl (36) show sub-micromolar inhibition (Table 5, FIG. 9). From the para-substituted benzyl derivatives of both the parent compounds 3 and 4, these analogs fail to show potent inhibition when compared to the analogs of ortho- and meta-position.

Effect of Bulkier Substituents

To examine the effect of bulkier substituent on the parent compound 4, the 4-biphenyl (48) derivative, and 1-naphthyl derivative (49) were synthesized. Derivative 48, similar to derivative 30, did not result in the intended improvement in the affinity (Table 4, FIG. 8). Surprisingly, the derivative 49 not only showed a great enhancement in inhibition, but also showed better inhibition than derivative 14.

Effect of Hydrophilic Functional Group

Figure 10:
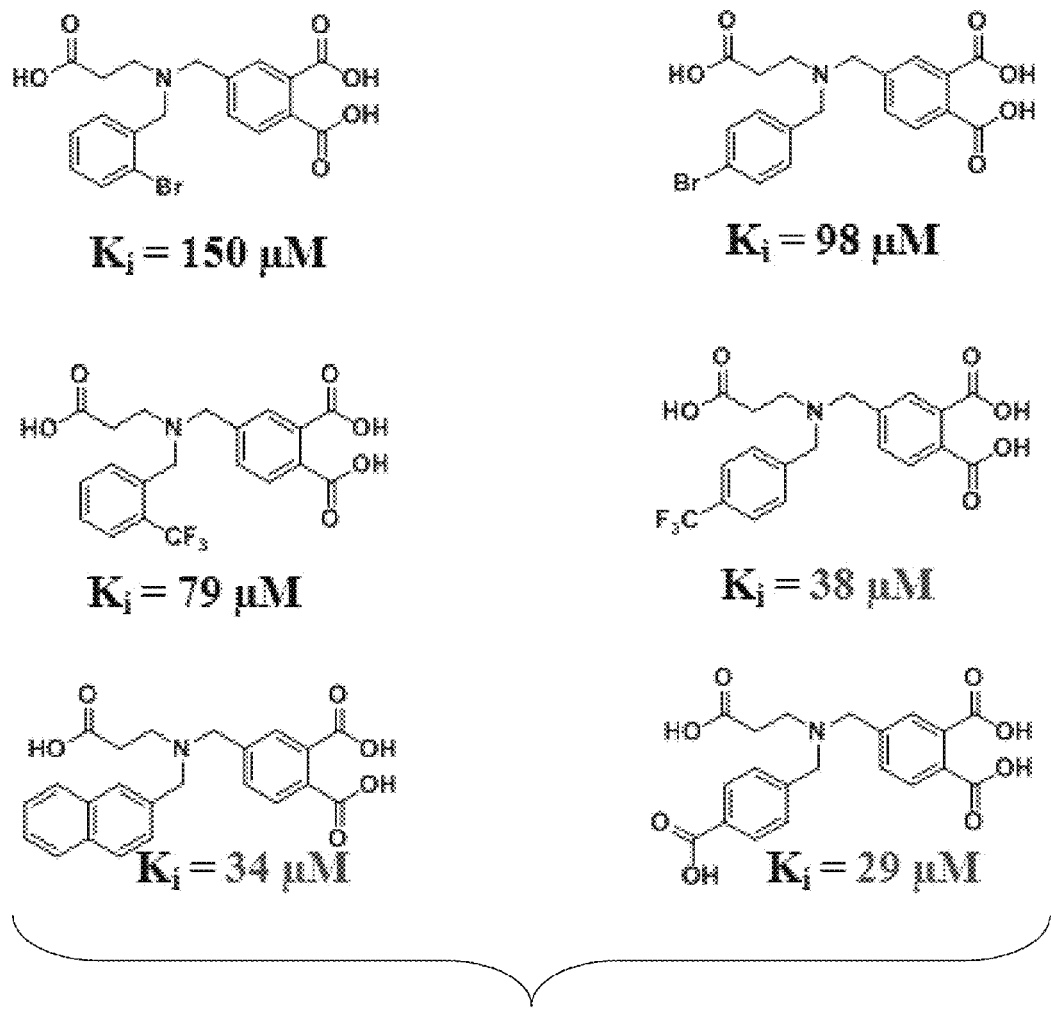
FIG. 10: Non-limiting examples of ANAT inhibitor phthalate derivatives.

Given the observed significance of electrostatic interaction of the p-carboxyl derivative 31, a similar analog of the longer chain parent compound 4 with a carboxyl group para to the benzyl group (50) was synthesized. This derivative shows a 100-fold improvement in the affinity with $K_i$ value of 29 µM (Table 5, FIG. 9). This compound is clearly the best ANAT inhibitor from the phthalate series of tested inhibitors described in this Example. FIG. 10 shows six of the best ANAT inhibitor compounds tested.

Incorporation of Bifunctional Groups

The two best hits from the phthalate series of compounds are the 1-napthyl derivative (49) and the 4-carboxy benzyl derivative (50) with $K_i$ values of 34 and 29 µM, respectively. From these results, it is evident that affinity of the inhibitor is greater for the 1-naphthyl and the p-carboxyl group. This observation leads to combining the features of both 1-naphthyl and the p-carboxyl group in a single molecule. Therefore, the 4-carboxy-1-napthyl derivative (51) was synthesized. Unfortunately, this compound did not show the desired level of potency, with $K_i$ value of 187 µM (Table 3, FIG. 9). Without wishing to be bound by theory, it is believed that the reduced affinity for this charged naphthyl derivative is due to the orientation of this side chain in a different binding position.

Materials and Methods

Enzyme Production and Activity Assay

Recombinant maltose-binding protein-human aspartate N-acetyltransferase (MBP-ANAT) fusion enzyme was expressed and purified as described in U.S. Provisional Patent Application No. 62/216,700. Briefly, NiCo21(DE3) competent *E. coli* cells (New England Biolabs, Ipswich, Mass.) were transformed with an MBP-ANAT-his construct and selected on LB plates with 30 µg/ml kanamycin. Colonies from these plates were used to inoculate starter cultures in LB media. After diluting each starter culture by 100-fold in 1 L of LB media, cell growth was continued for about 2 hours at 37° C. until A600 reached 0.6. IPTG was then added to a final concentration of 0.5 mM, and protein expression was induced at 16° C. for 20 hours. To purify MBP-ANAT, a Ni Sepharose 6 Fast Flow column (GE Healthcare, Pittsburgh, Pa.) was equilibrated with Buffer A (20 mM potassium phosphate, pH 7.4, 300 mM sodium chloride, 10% glycerol, and 20 mM imidazole). Cell lysate was loaded on to the column and partially purified ANAT was then eluted with a linear gradient of Buffer B (buffer A containing 400 mM imidazole). The active fractions were pooled and loaded onto an amylose column and highly purified ANAT fusion was then obtained by elution with a 0-10 mM linear maltose gradient. ANAT activity was measured by an established DTNB-based assay using a SpectraMax 190 spectrophotometer plate reader (Molecular Devices, CA). A typical activity assay contains 20 mM HEPES, pH 7.4, 150 mM NaCl, 5% glycerol, 40 µM DTNB, 40 µM acetyl-CoA, and 2 mM L-aspartate in a total volume of 200 µl. Reaction was monitored at 412 nm (c=14.15 mM cm$^1$) for at least 15 minutes.

Compound Library Screening

Three different compound libraries were used for initial screening of ANAT inhibitors. These small compound libraries were assembled in-house: an amino acids library contained 96 compounds, a metabolite library contained 96 compounds, and a second amino acids library contained 64 compounds. An additional constrained analogs library contained 77 compounds that were purchased from commercial sources. Once the dioic acid core structure was identified as a viable inhibitor of ANAT, an extended library of dioic acid compounds was synthesized for testing and optimization.

General Phthalate Derivative Procedures

Phthalate analogs were introduced into the ANAT inhibitor design. This core structure allowed additional structural elaborations and added complexity to the inhibitor structure. To produce the parent compounds, the protocol described above in Example I was followed. The synthetic route illustrated in Scheme 1A (FIG. 2A) was utilized to produce the amine-containing 4-(carboxymethylaminomethyl) and 4-(2-carboxyethylaminomethyl)phthalate analogs 3 and 4, respectively, as well as the amine-containing alanine methyl ester or serine methyl ester analogs 5 and 6. A similar protocol was used to produce compound 9, which is analogous to compound 3 except for the position of side chain and amine being protected (Scheme 2, FIG. 3). The affinities of these parent compounds were examined against ANAT and then improved through the production of an extensive series of derivatives introduced at the secondary amine.

Certain embodiments of the compounds, compositions, and methods disclosed herein are defined in the above examples. It should be understood that these examples, while indicating particular embodiments of the invention, are given by way of illustration only. From the above discussion and these examples, one skilled in the art can ascertain the essential characteristics of this disclosure, and without departing from the spirit and scope thereof, can make various changes and modifications to adapt the compositions and methods described herein to various usages and conditions. Various changes may be made and equivalents may be substituted for elements thereof without departing from the essential scope of the disclosure. In addition, many modifications may be made to adapt a particular situation or material to the teachings of the disclosure without departing from the essential scope thereof.

What is claimed is:

1. A composition comprising Formula II:

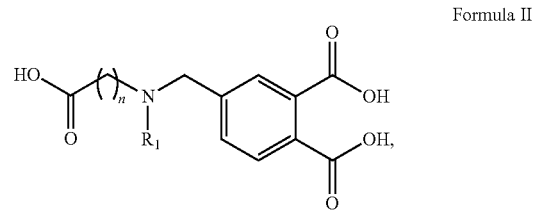

Formula II wherein:

n is either 1 or 2, and $R_1$ is substituted or unsubstituted aryl, alkyl, aralkyl, or aryloxy;

and salts, stereoisomers, racemates, solvates, and hydrates thereof.

2. The composition of claim 1, wherein $R_1$ is benzyl.

3. The composition of claim 1, wherein $R_1$ is naphthyl.

4. The composition of claim 1, wherein n is 1, and $R_1$ is aryl or aryloxy.

5. The composition of claim 1, wherein n is 2, and $R_1$ is aryl or aryloxy.

6. The composition of claim 1, wherein $R_1$ is biphenyl.

7. A composition comprising Formula III:

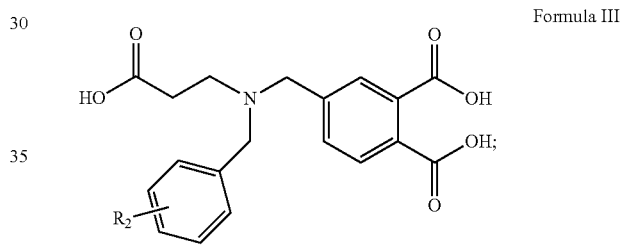

Formula III wherein $R_2$ is H, halo or substituted or unsubstituted aryl, alkyl, or carboxyl, provided, however, that when $R_2$ is aryl, the aryl forms a fused bicyclic ring.

8. A composition comprising Formula III:

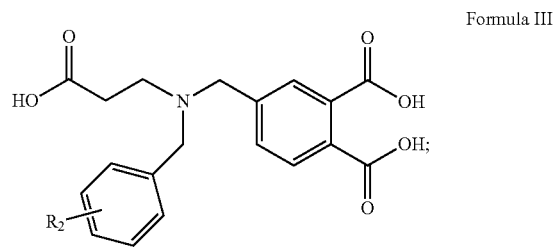

Formula III wherein $R_2$ is hydrogen, a straight or branched alkyl having from 1 to 6 carbons, a halogen, a halogenated alkyl having from 1 to 6 carbons, a halogenated alkoxy, or a substituted or unsubstituted cyclic alkyl.

9. The composition of claim 8, wherein $R_2$ is selected from the group consisting of: H, 4-bromo, 4-methyl, 4-trifluoromethyl, 4-trifluoromethoxy, 4-difluoromethoxy, 4-tert-butyl, 4-(2-perfluoropropyl), 4-phenyl, 4-((2-benzyl)vinyl), and 4-trifluoromethyl.

10. The composition of claim 1, wherein the composition consists essentially of a sodium salt of Formula II.

11. A pharmaceutical composition comprising:
a composition of claim 1; and
a pharmaceutically acceptable excipient, diluent, or carrier.

12. A method of making a composition of claim 1, the method comprising:
i) esterifying a dicarboxylic methylphthalate to produce a methylphthalate dimethyl ester;
ii) bromonating the methylphthalate dimethyl ester to produce a bromomethylphthalate dimethyl ester by either:
a) coupling the bromomethylphthalate dimethyl ester with glycine methyl ester to produce an esterified N-carboxymethyl dicarboxybenzylamine; or,
b) coupling the bromomethylphthalate dimethyl ester with β-alanine methyl ester to produce an esterified N-carboxyethyl dicarboxybenzylamine;
and,
iii) reacting the bromomethylphthalate dimethyl ester with an alkyl halide or a benzyl halide to produce an ester compound.

13. A method of inhibiting ANAT activity in a cell, the method comprising:
administering a composition of claim 1 to a cell, and inhibiting ANAT activity in the cell.

14. The composition of claim 1, wherein the compound is selected from:
N-carboxymethyl-3,4-dicarboxybenzylamine;
N-carboxyethyl-3,4-dicarboxybenzylamine;
N-((2-methyl)carboxymethyl)-3,4-dicarboxybenzylamine;
N-((2-hydroxymethyl)carboxymethyl)-3,4-dicarboxybenzylamine;
N-methyl, N-carboxymethyl-2,3-dicarboxybenzylamine;
N-methyl, N-carboxymethyl-3,4-dicarboxybenzylamine;
N-allyl, N-carboxymethyl-3,4-dicarboxybenzylamine;
N-acetonitrile, N-carboxymethyl-3,4-dicarboxybenzylamine;
N-benzyl, N-carboxymethyl-3,4-dicarboxybenzylamine;
N-(1-naphthyl)-N-carboxymethyl-3,4-dicarboxybenzylamine;
N-(2-naphthyl)-N-carboxymethyl-3,4-dicarboxybenzylamine;
N-(ethylmorpholino)-N-carboxymethyl-3,4-dicarboxybenzylamine;
N-(4-biphenyl)-N-carboxymethyl-3,4-dicarboxybenzylamine;
N-(2-bromobenzyl)-N-carboxymethyl-3,4-dicarboxybenzylamine;
N-(3-bromobenzyl)-N-carboxymethyl-3,4-dicarboxybenzylamine;
N-(4-bromobenzyl)-N-carboxymethyl-3,4-dicarboxybenzylamine;
N-(2-methylbenzyl)-N-carboxymethyl-3,4-dicarboxybenzylamine;
N-(3-methylbenzyl)-N-carboxymethyl-3,4-dicarboxybenzylamine;
N-(4-methylbenzyl)-N-carboxymethyl-3,4-dicarboxybenzylamine;
N-(2-trifluoromethylbenzyl)-N-carboxymethyl-3,4-dicarboxybenzylamine;
N-(3-trifluoromethylbenzyl)-N-carboxymethyl-3,4-dicarboxybenzylamine;
N-(4-trifluoromethylbenzyl)-N-carboxymethyl-3,4-dicarboxybenzylamine;
N-(2-trifluoromethyoxybenzyl)-N-carboxymethyl-3,4-dicarboxybenzylamine;
N-(3-trifluoromethoxybenzyl)-N-carboxymethyl-3,4-dicarboxybenzylamine;
N-(4-trifluoromethoxybenzyl)-N-carboxymethyl-3,4-dicarboxybenzylamine;
N-(4-difluoromethoxybenzyl)-N-carboxymethyl-3,4-dicarboxybenzylamine;
N-(4-carboxybenzyl)-N-carboxymethyl-3,4-dicarboxybenzylamine;
N-(4-carboxamidebenzyl)-N-carboxymethyl-3,4-dicarboxybenzylamine;
N-(4-t-butylbenzyl)-N-carboxymethyl-3,4-dicarboxybenzylamine;
N-(4-(2-perfluoropropyl))-N-carboxymethyl-3,4-dicarboxybenzylamine;
N-(4-bromobenzyl)-N-carboxyethyl-3,4-dicarboxybenzylamine;
N-(4-trifluoromethylbenzyl)-N-carboxymethyl-3,4-dicarboxybenzylamine; or,
N-acetal-N-carboxymethyl-3,4-dicarboxybenzylamine.

* * * * *